United States Patent [19]
Kovalcheck

[11] Patent Number: 5,549,542
[45] Date of Patent: Aug. 27, 1996

[54] DEFLECTABLE ENDOSCOPE

[75] Inventor: Steven W. Kovalcheck, San Diego, Calif.

[73] Assignee: Life Medical Technologies, Inc., Salt Lake City, Utah

[21] Appl. No.: 977,875

[22] Filed: Nov. 17, 1992

[51] Int. Cl.⁶ .................................................. A61B 1/008
[52] U.S. Cl. ........................................... 600/146; 600/150
[58] Field of Search ....................... 158/4, 6, 656–658; 604/85, 280; 600/146, 150

[56] References Cited

U.S. PATENT DOCUMENTS

| | | |
|---|---|---|
| D. 254,270 | 2/1980 | Ziegler . |
| 3,557,780 | 1/1971 | Sato . |
| 3,572,325 | 3/1971 | Bazell et al. . |
| 3,610,231 | 10/1971 | Takahashi et al. . |
| 3,788,303 | 1/1974 | Hall . |
| 3,799,152 | 3/1974 | Kim . |
| 4,038,987 | 8/1977 | Komiya . |
| 4,108,211 | 8/1978 | Tanaka . |
| 4,178,920 | 12/1979 | Cawood, Jr. et al. . |
| 4,207,873 | 6/1980 | Kruy . |
| 4,290,421 | 9/1981 | Siegmund . |
| 4,327,711 | 5/1982 | Takagi . |
| 4,351,323 | 9/1982 | Ouchi et al. . |
| 4,432,349 | 2/1984 | Oshiro . |
| 4,436,087 | 3/1984 | Ouchi . |
| 4,499,895 | 2/1985 | Takayama . |
| 4,503,842 | 3/1985 | Takayama . |
| 4,559,928 | 12/1985 | Takayama . |
| 4,588,294 | 5/1986 | Siegmund . |
| 4,651,718 | 3/1987 | Collins et al. . |
| 4,686,963 | 8/1987 | Cohen et al. . |
| 4,688,555 | 8/1987 | Wardle . |
| 4,726,355 | 2/1988 | Okada . |
| 4,748,969 | 6/1988 | Wardle . |
| 4,762,118 | 8/1988 | Lia et al. . |
| 4,762,119 | 8/1988 | Allred, III et al. . |
| 4,770,443 | 9/1988 | Yamamoto . |
| 4,774,949 | 10/1988 | Fogarty . |
| 4,784,117 | 11/1988 | Miyazaki . |
| 4,787,369 | 11/1988 | Allred, III et al. . |
| 4,802,461 | 2/1989 | Cho . |
| 4,807,598 | 2/1989 | Hasegawa . |
| 4,817,630 | 4/1989 | Schintgen et al. . |
| 4,834,518 | 5/1989 | Barber . |
| 4,836,189 | 6/1989 | Allred, III et al. . |
| 4,852,550 | 8/1989 | Koller et al. . |
| 4,861,336 | 8/1989 | Helzel . |
| 4,873,965 | 10/1989 | Danieli ....................................... 128/6 |
| 4,881,524 | 11/1989 | Boebel et al. . |

(List continued on next page.)

FOREIGN PATENT DOCUMENTS

| | | |
|---|---|---|
| 0306723 | 8/1988 | European Pat. Off. . |
| 0389453 | 3/1990 | European Pat. Off. . |
| 0455188 | 4/1991 | European Pat. Off. . |
| 0448284 | 3/1992 | European Pat. Off. . |
| 145056 | 11/1980 | Germany . |
| 3602092 | 7/1986 | Germany . |
| 3504824 | 8/1986 | Germany . |
| 61-118712 | 6/1986 | Japan . |
| 2109241 | 6/1983 | United Kingdom . |
| 2138687 | 10/1984 | United Kingdom . |
| 2151142 | 7/1985 | United Kingdom . |

*Primary Examiner*—Richard J. Apley
*Assistant Examiner*—John Mulcahy
*Attorney, Agent, or Firm*—Knobbe, Martens, Olson & Bear

[57] ABSTRACT

A minimally intrusive endoscope having a deflectable tip. A remotely bendable section adjacent a distal viewing tip enables movement of the tip between a neutral position and angularly disposed positions. A deflection control lever on a proximal control member causes deflection of the viewing tip by means of two sets of operating cables which are operatively connected at one end to the control member and at the other end to axially spaced locations along the controllably bendable section. The control member includes a mechanism for sequentially displacing cables within each set. The operating cables are constructed of flat ribbons to increase their flexibility in the bending plane while still providing axial strength. The wires are closely encased in an oval-shaped sheath along the length of the endoscope.

36 Claims, 10 Drawing Sheets

U.S. PATENT DOCUMENTS

| | | |
|---|---|---|
| 4,895,431 | 1/1990 | Tsujiuchi et al. . |
| 4,911,148 | 3/1990 | Sosnowski et al. . |
| 4,919,112 | 4/1990 | Siegmund . |
| 4,930,521 | 6/1990 | Metzger et al. . |
| 4,941,454 | 7/1990 | Wood et al. . |
| 4,941,457 | 7/1990 | Hasegawa . |
| 4,949,706 | 8/1990 | Thon . |
| 4,994,910 | 2/1991 | Williams . |
| 4,996,974 | 3/1991 | Ciarlei . |
| 5,083,549 | 1/1992 | Cho et al. . |
| 5,176,126 | 1/1993 | Chikama . |
| 5,257,618 | 11/1993 | Kondo . |
| 5,271,381 | 12/1993 | Ailinger et al. . |
| 5,271,382 | 12/1993 | Chikama . |

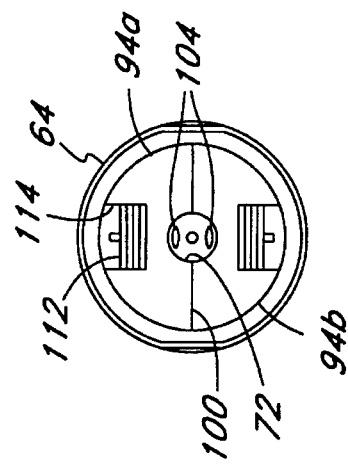
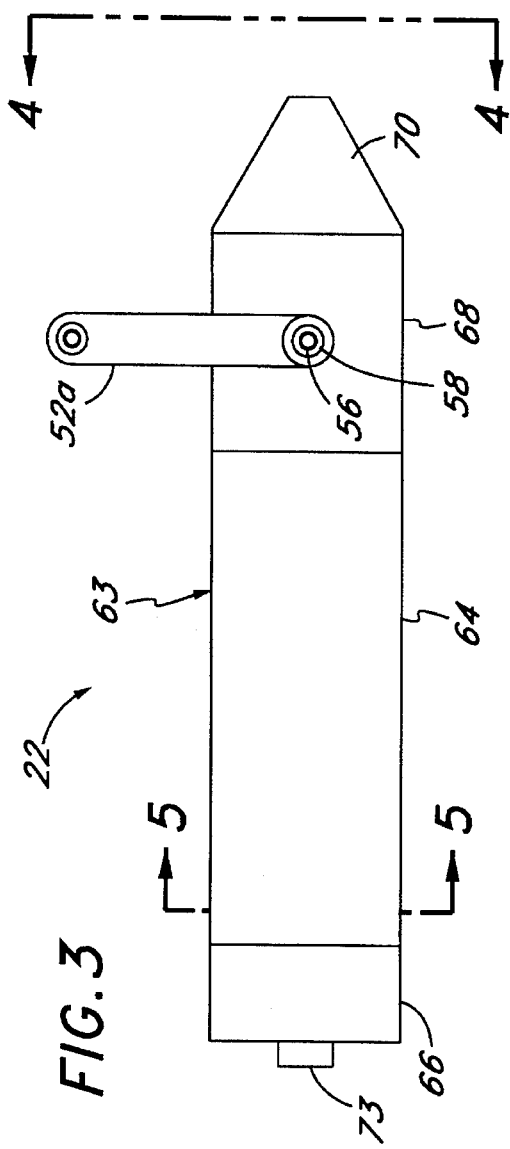
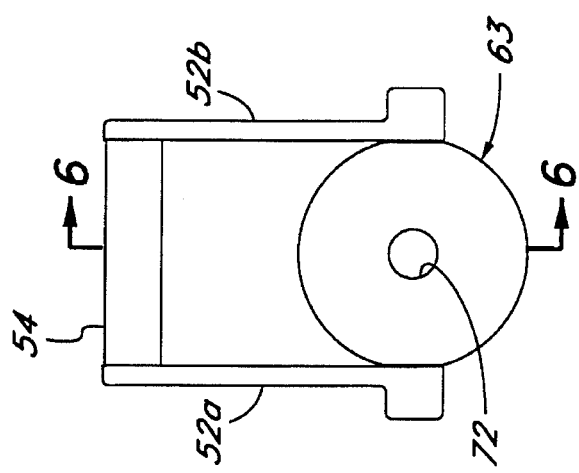

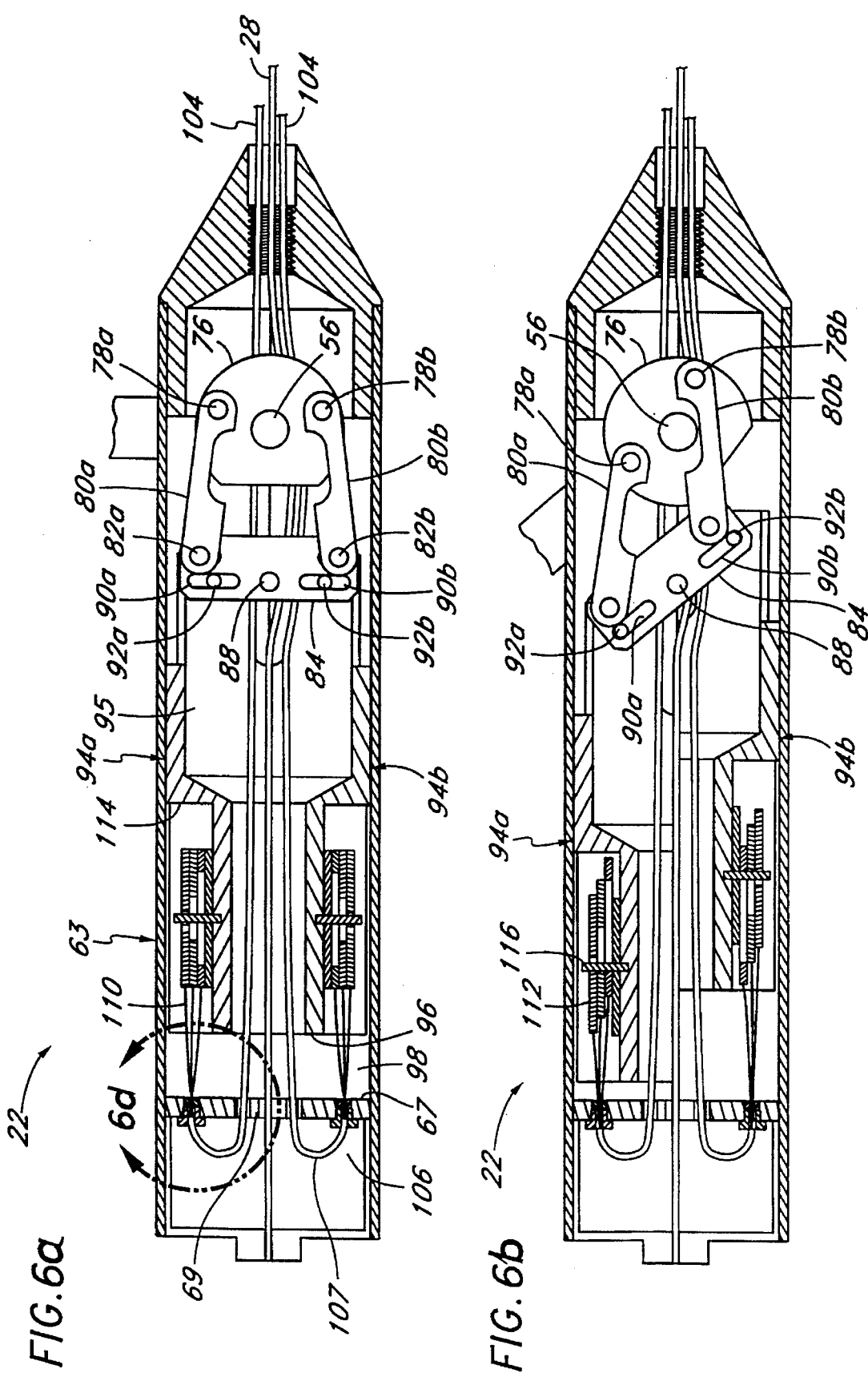

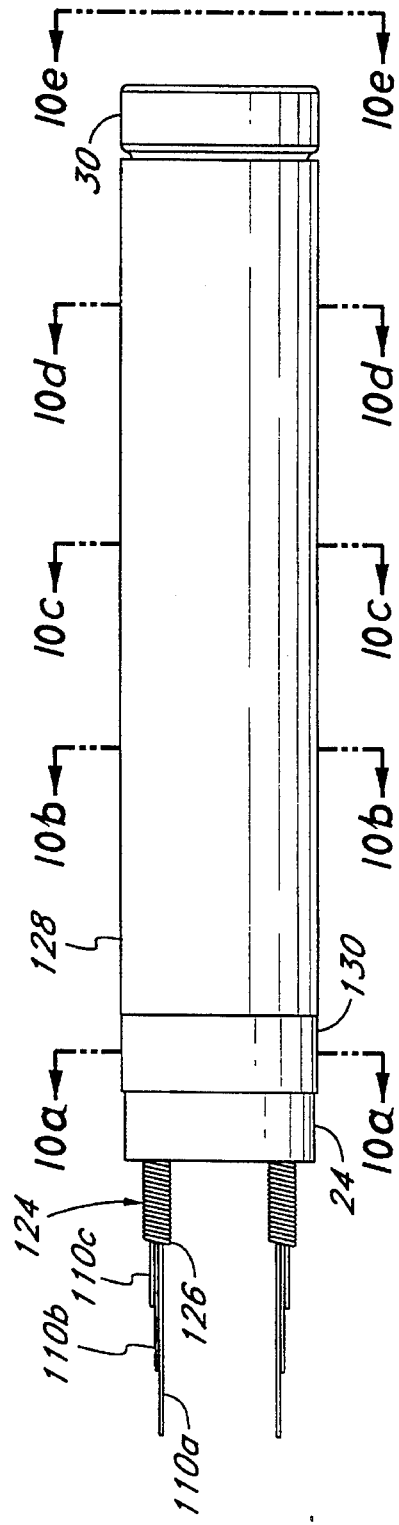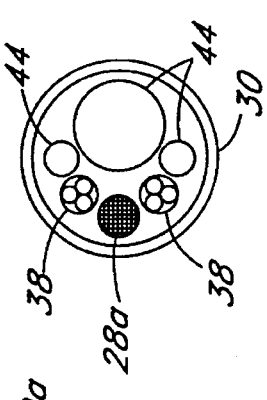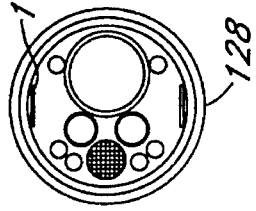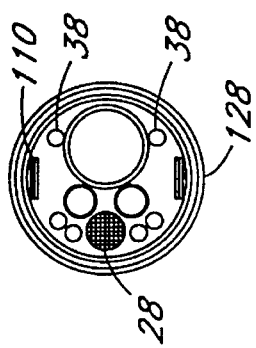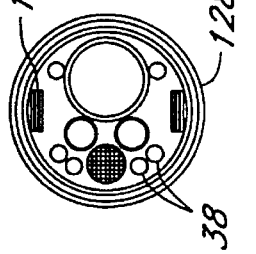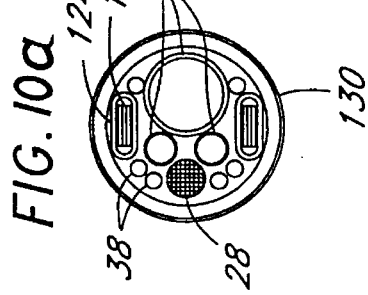

DEFLECTABLE ENDOSCOPE

BACKGROUND OF THE INVENTION

This invention relates to an elongated flexible inspection system for use in both industrial and medical applications and, more particularly, to a steering mechanism for endoscopes.

Endoscopes are well known optical imaging devices used for viewing objects within cavities or the internal surfaces of cavities, with additional capabilities of providing channels for insertion of devices to act upon or treat conditions of interest. While the present invention has application in many fields, it has particular relevance to the medical field, wherein flexible steerable endoscopes are employed to view and treat deep and circuitous passages of the human body.

A steerable endoscope generally comprises an elongated insertion tube having a distal passively bendable portion and an optional rigid portion, a controllably bendable segment at the distal end of the passively bendable portion, a viewing tip at the extreme distal end of the bendable segment, a control member at the proximal end of the elongated tube for remotely steering the bendable segment and a fused or loose bundle of optical fibers extending from the rear end of the control member to the viewing tip. Optical fibers that transmit light and various conduits may be provided for surgical devices or fluid paths within the insertion tube. Usually, one or two pairs of control cables, depending on the number of planes of bending, extend through the controllably bendable section and the remainder of the insertion tube and connect with a steering control mechanism in the control member in order to remotely deflect the distal bendable section. One or both pairs of these cables are longitudinally displaced (pulled or pushed) to generate a bending moment in the steering section and deflect the viewing tip for inspection of an object.

Non-medical devices having structure closely resembling endoscopes exist and share identical design problems. For example, borescopes are used for visual inspection of mechanical assemblies, such as the interior of a jet engine or turbine, where it would be difficult or impossible to view internal elements. The borescope must be insertable into narrow crooked passageways, the associated steering and bending difficulties paralleling those of endoscopes.

In a steerable endoscope or borescope, opposing steering cables are displaced to deflect the distal tip. These cables are oppositely longitudinally displaced, that is, as one cable is pulled away from the bending section, the diametrically opposed cable moves toward the bending section to provide a moment about the tip. The cables are attached to the inner wall of the distal end of the endoscope so that when pulled, the bending moment applied is proportional to the pulling force multiplied by the distance from the centerline of the section to which the cables attach.

There are two general methods of inserting endoscopes into the body: one in which an incision is made to access a cavity such as a blood vessel or the abdominal wall, and a second where the endoscope is inserted through a natural aperture, such as the nose, mouth, urethra or rectum. A steerable endoscope is typically inserted into a vessel or body cavity of a patient for visual inspection of tissues within the cavity. For example, an endoscope can be inserted into the colon via the rectum, into a lung via the trachea or into the heart via the femoral artery. Because the various portals into the body comprise narrow, circuitous passageways, the steering section must be bendable rather precisely, and as close to the viewing tip as possible, to navigate the passageway without damaging the patient's tissues.

The current trend in medicine is toward minimally invasive surgical techniques, and in applications such as neurosurgery, obstetrical/gynecological procedures, cardiovascular surgery, et al., there is a demand for smaller and smaller diameter endoscopes. To produce the necessary bending moments in a small diameter endoscope, the force applied by the pulling cables becomes extreme, as the bending moment arm, or distance from the centerline of the section to which the cables attach, has been reduced. Unfortunately, it is not possible to simply increase the scale of the pulling cables to compensate for the increased forces. If the cables were allowed to be increased to take added load, the available space within the smaller diameter insertion tube would be reduced resulting in less room for the fiber optics and conduits provided for surgical devices or fluid paths.

The stiffness of the controllably bendable section and inner components is another factor directly affecting the amount of force necessary to deflect the viewing tip. Many endoscopes contain fused silica fiber optic bundles which, though bendable, represent a primary source of stiffness. Fused bundles generally have comparable picture resolution when compared with loose fiber optic bundles, yet have been adopted for their cost savings in manufacturing. Furthermore, individual fibers in loose bundles may be separately adversely affected by excessive bending whereas the fibers in a fused bundle all remain functional up until a bend limit is reached for the entire unit. Despite certain advantages of fused bundles, the fibers are held together within a hardened adhesive, and thus are substantially stiffer than loose bundles, resulting in a significant addition to the strength requirements of the pulling cables.

There are recurring problems which result when excessive stresses are applied to the operating cables by the control mechanism. In an extreme situation, the cable can break or, in a less extreme situation, the cable can be permanently stretched. In the former instance, the endoscope is rendered useless until the cable has been replaced. In the latter instance, the endoscope loses a portion of its original deflection capability, making it necessary to take up the slack of the stretched cable or recalibrate the instrument. Also, if the cables on one side stretch, the deflectable portion of the endoscope will not return to a straightened form when it is relaxed. In the case of reusable endoscopes, it is necessary to open the instrument, usually at the factory or at a well-equipped service center, and perform the necessary servicing to return the instrument to its nominal operating condition. Of course, if a problem arises in the midst of a surgical procedure, the surgery may be interrupted and delayed for critical minutes while a working endoscope is re-inserted into the patient.

To repeatedly and efficiently cause a particular deflection angle in deflectable endoscopes, the stress developed in the control cables must be less than the yield stress of the wire. To ensure that this criteria is satisfied, some devices incorporate slip clutches, force distributing or force limiting systems to avoid overly stressing the control wires. Devices of this kind are shown in U.S. Pat. Nos. 4,762,118, 4,762,119 and 4,787,369. Other devices, such as in U.S. Pat. No. 4,688,555, include a cable tensioner to guard against high loads and take up cable slack.

Concurrently, a balance has been pursued by numerous designers and inventors whereby the material properties, configurations and dimensions of the component parts of catheters and endoscopes have been adjusted to keep the induced wire stress below the yield stress of the wire for given deflection angles. These endeavors have seen the development of highly elastic polymers, the use of loose fiber optic bundles, the adoption of unique tubular geometric profiles, e.g., notched tubes, and the replacement of deformable, i.e., elastic, materials with articulating disks or vertebrae.

It appears that with every new breakthrough, a demand for deflectable tubular devices of even smaller diameter presents itself. With the development of novel tube or conduit constructions and the use of highly elastic materials, extrapolation of existing designs to even smaller endoscopes has resulted in a tremendous amount of stress being placed upon the actuating wires and the connection of these wires to the tubular device when significant deflection is required. This stress has resulted in the frequent occurrence of device failure due to either load wire fatigue, stretching and breakage or to bond failures between the load wire and the tubular device. As endoscopes become smaller in cross section, a practical limit is reached whereby the only way to insure that the wires do not fail is to reduce the tension on the wires, thereby reducing the maximum angle of deflection.

Therefore, there is a need for a steering mechanism for microendoscopes which reduces the possibility of cable fatigue, stretching or breakage while retaining desirable deflection capabilities.

SUMMARY OF THE INVENTION

The present invention is directed toward an inspection instrument having a generally elongated flexible body extending between a proximal control member and a distal viewing tip. A controllably bendable section, which is adjacent to the viewing tip, enables movement of the tip between a neutral position and a plurality of angularly disposed positions. A deflection control lever on the control member causes deflection of the viewing tip by means of two sets of operating wires which are operatively connected at their opposite ends to the control member and to the controllably bendable section. Each set of operating wires includes a plurality of wires which terminate at different locations along the length of the controllably bendable section.

In accordance with a preferred embodiment of the present invention there are two sets of three operating wires. Each set of three wires lies along the diametrically opposite side of the endoscope from the other and thus, bending takes place in one of two directions in a single plane. The proximal ends of each of the six control wires are connected to a control mechanism within the control member for applying linear displacement along the axis of the tubular endoscope. The distal ends of each of the six operating wires terminate at axially spaced locations along the inner wall of a controllably bendable section of the endoscope.

Looked at from a different perspective, there are three pairs of two wires, each pair terminating at the same location on diametrically opposite sides of the endoscope. A first pair of wires, one wire on each side of the endoscope, terminates at the extreme distal end, just behind the viewing tip, to provide controllable bending at this location. A second pair of operating wires, one on each side of the endoscope, terminates approximately a third of the way back along the controllably bendable section from the viewing tip, providing bending control at a second location. A third pair of operating wires, one on each side of the endoscope, terminates still further proximally from the viewing tip to provide a third controllable bending location. The locations of the termination points of the operating wires is not limited to being equally spaced apart along the controllably bendable section as described, such a spacing is used as a representative example only.

To controllably bend the distal tip, one or more wires within one set along one side of the endoscope are pulled, while the diametrically opposed wire for each pair of wires which terminates at the same location is pushed, or fed, toward the distal tip. By sequentially, or otherwise proportionally, displacing one or more of the wires in a set on one side with respect to the others in the same set on the same side, the controllably bendable section can articulate in any number of curvilinear configurations. Advantageously, the use of three parallel wires on each pulling side reduces the load demand generated within any one wire, for a predetermined deflection angle, thus reducing stress in the wire.

In a preferred embodiment of the present invention, the three operating wires are constructed of flat ribbons which possess equivalent tensile properties as round wires with equivalent cross-sectional area. Advantageously, however, the flat wires possess far greater flexibility in the bending plane of the articulated endoscope than round wires. Furthermore, the three control ribbons on each side of the endoscope are disposed on top of one another to present a reduced radial projection within the insertion tube, thereby conserving inner lumen space of the endoscope for use as a passageway for fiber optics, fluid conduits or channels for surgical devices.

From the control mechanism distally to the controllably bendable section, the three control ribbons on each side of the endoscope are encased in an elongated oval-shaped sheath. This sheath acts to protect and constrain the wires along the length of the endoscope. Advantageously, the sheath comprises an oval-shaped tightly-wrapped coil which closely surrounds the three flat ribbons.

The distal ends of the sheaths are firmly attached to the proximal end of a flexible member mounted within the controllably bendable section. The sheath and ribbons extend through the center of the control member in a proximal direction and loop around towards the distal direction where the sheath is retained in a tight fitting. The ribbons emerge from the sheath to be connected to the control mechanism. In this respect, the proximal ends of the sheaths are firmly attached a fixed distance from the control mechanism. Clearance is provided within the sheaths for axial movement of the ribbons within the sheath. Actuation of the control mechanism displaces the ribbons with respect to the sheath to remotely control the bendable section.

The control ribbons firmly attach to axially spaced points along the inner surface of a tubular flexible member disposed within the controllably bendable section of the endoscope. The flexible member provides hoop strength to the controllably bendable section to prevent collapse while minimizing resistance to bending. Advantageously, the flexible member has discrete attachment regions for mounting the control ribbons separated by regions of increased flexibility in the bending plane. The structure of the flexible member preferably provides a predetermined level of axial or column strength to maintain a consistent distance between the attachment regions during deflection.

In a preferred embodiment, the flexible member comprises a variable pitch coil spring. The spring includes at least three axially spaced regions of tightly wound loops separated by regions of loosely wound loops. The control ribbons weld, solder or braze to the regions of closely-wound loops, while the intermediate loosely wound regions provide enhanced flexibility. In one embodiment, one or more axially disposed spines may be attached to each tightly wound region to maintain a consistent distance between the tightly wound regions during deflection of the bendable section.

In another preferred embodiment, the flexible member comprises a coiled ribbon or flat wire. The control ribbons attach to the coiled flat wire at locations axially spaced apart. The coiled flat wire is prestretched to provide a predetermined axial gap between adjacent loops to enhance flexibility.

According to a preferred embodiment of the present invention, the hand or machine operated control mechanism displaces one of the three wires first, then the second wire, then the third wire, sequentially. In the situation where the first wire is connected to the extreme distal portion of the controllably bendable section, the first stage of operation will bend the farthest distal tip. Further actuation will cause the middle portion of the controllably bendable section to articulate and, consequently, actuating the third wire will cause the most proximal section of the bendable section to deflect. As the second and third control wires are being actuated, and the endoscope is bent farther, the additional stress on the first wire is minimal and thus, the possibility of tensile yield or fracture is greatly reduced, while useful deflection angles are attained.

BRIEF DESCRIPTION OF THE DRAWINGS

FIG. 3 is a side elevational view of the control member of the endoscopic system of FIG. 2.

FIG. 4 is a front elevational view of the control member taken along line 4—4 FIG. 3.

FIG. 5 is a cross-sectional view of the control member taken along line 5—5 of FIG. 3.

FIGS. 6a, 6b and 6c are partial sectional views of the control member taken along line 6—6 of FIG. 4 and showing the steering control mechanism.

FIG. 6d is a detail of the control mechanism of FIG. 6a.

FIG. 9 is a detail of the distal controllably bendable section of the preferred endoscopic system shown in FIG. 1.

FIG. 10a is a cross-sectional view of the passively bendable portion of the insertion tube taken along line 10a—10a of FIG. 9.

FIGS. 10b, 10c and 10d are cross-sectional views of the controllably bendable section taken along corresponding lines of FIG. 9.

FIG. 10e is an end elevational view of the viewing tip taken along line 10e—10e of FIG. 9.

DESCRIPTION OF THE PREFERRED EMBODIMENTS

Figure 1:
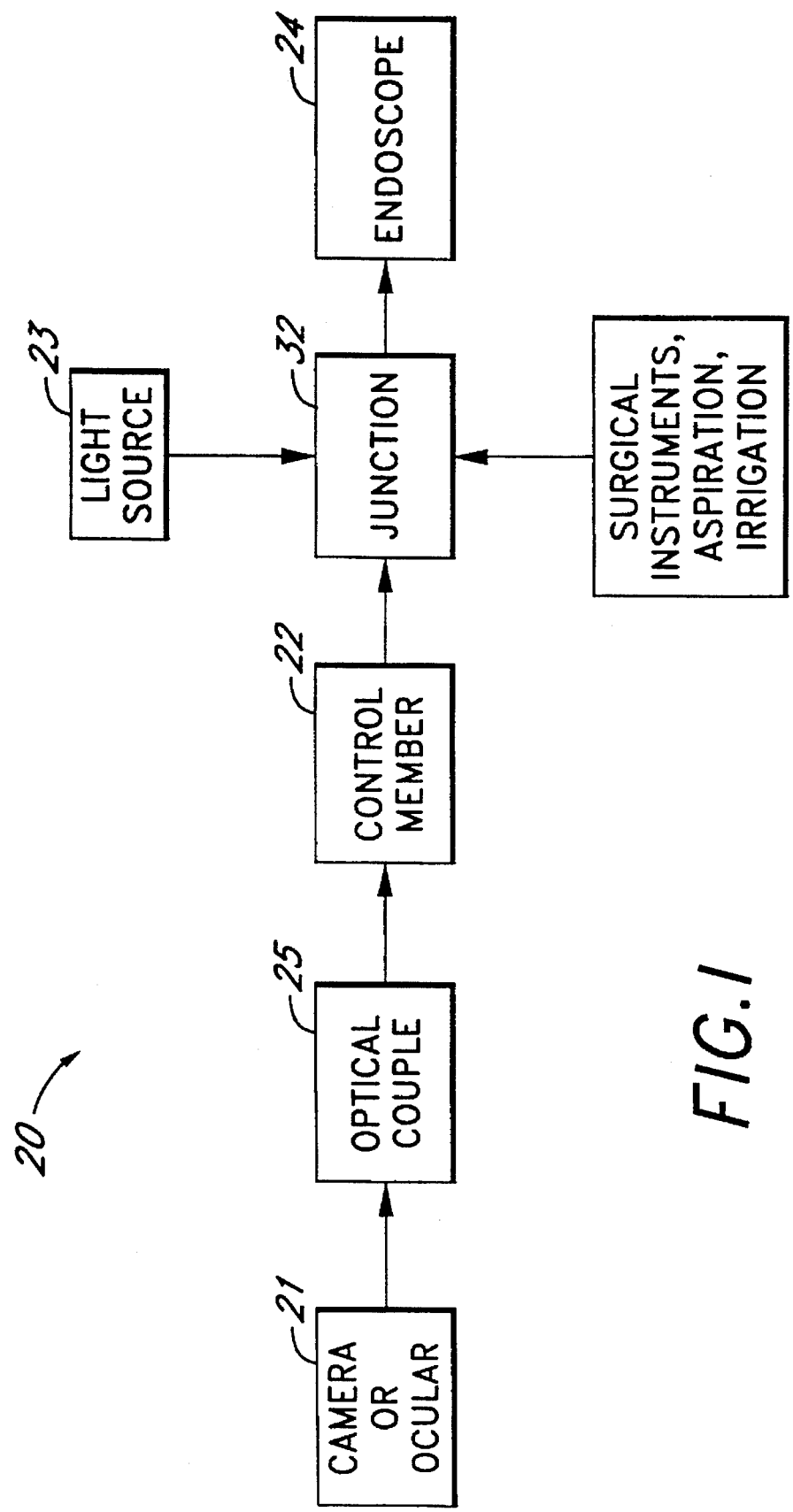
FIG. 1 is a schematic diagram showing an endoscopic surgical system as in the present invention.

A system 20 for endoscopic surgery is shown schematically in FIG. 1. A camera or ocular 21 allows a surgeon to view objects within a patient (not shown) close to the distal end of an endoscope or insertion tube 24. In this respect, a light source 23 illuminates the object via optical fibers extending through a junction member 32 to the distal end of the insertion tube 24. The images then transmit proximally via optical fibers passing through the insertion tube 24, junction member 32, a control member 22 and an optical couple 25 to be viewed directly through the ocular 21, or indirectly on a video monitor connected to the camera. Optionally, the surgeon may actively operate using a variety of elongated surgical instruments, and aspiration or irrigation means in communication with the object within the patient via working channels extending through ports in the junction member 32 and thereafter through the insertion tube 24.

Figure 2:
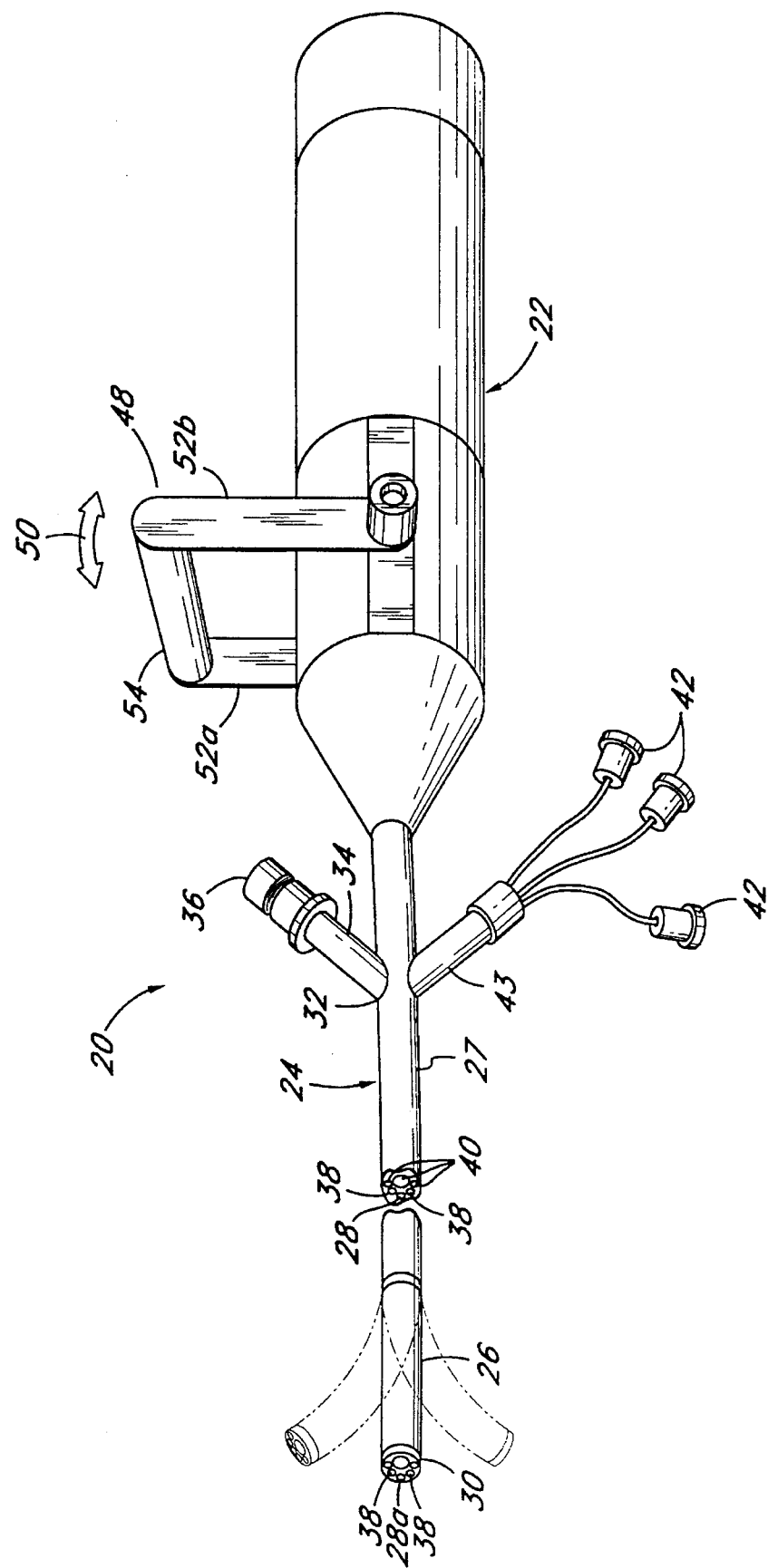
FIG. 2 is a perspective view of an endoscopic system as in FIG. 1 utilizing the preferred articulation mechanism of the present invention.

The steerable endoscopic system or endoscope 20 of the present invention, having an improved mechanism for reducing stress in the pull wires at predetermined deflection angles, is shown in FIG. 2. Although the present invention will be described with particular reference to an endoscope, it is well known in the art to incorporate facets of endoscopes into devices with industrial applications, such as a borescope, or to other similar devices, and the invention is not considered limited to endoscopes.

The endoscope 20 generally comprises the proximal control member 22 and the distal insertion tube 24 having a passively bendable portion 27 terminating at a controllably bendable segment or section 26 for navigating the distal end of the insertion tube through circuitous channels in a patient's body (not shown). The insertion tube 24 may also include a rigid portion (not shown) adjacent the control member 22. The insertion tube 24 preferably has an outer diameter of less than 4 mm for minimally invasive applications. The control member 22 is designed to be held in the hand of a surgeon for easy manipulation of the insertion tube 24. The controllably bendable section 26 of the insertion tube 24 terminates in a rigid distal viewing tip 30. A coherent bundle of optical fibers 28 runs the length of the endoscope 20 from the viewing tip 30 to the proximal end of the control member 22 where an eyepiece (not shown) may be disposed for viewing by a surgeon. A microlens 28a is disposed on the distal end of the coherent fiber optic bundle 28. Optionally, a second coherent bundle (not shown) of optical fibers provides stereo viewing capability.

Typically, the junction member 32 extends outwardly from the control member 22 and allows access to an inner lumen (not shown) of the insertion tube 24. In one embodiment, the junction member 32 forms a Y-shape to provide a first lumen access port 34 having a fitting 36 for six light source fibers 38, and a second lumen access port 40 having three luer-type fittings 42 and attached hoses 43 communicating with elongated flexible through channels 44 within the insertion tube 24. The through channels 44 provide operating conduits for elongated surgical devices, irrigation or suction, etc. The light fibers 38 and through channels 44 extend from the two ports 34, 40 and through to the viewing tip 30 to provide communication with the treatment site.

By inserting the tube 24 of the endoscope 20 within a patient's body and advancing the viewing tip 30 to a site for treatment, a surgeon may operate with the visual aid of the fiber optics 28 by manipulating instruments advanced through the channels 44 in the lumen of the insertion tube 24. In the presently preferred embodiment, three through channels 44 within the insertion tube 24 guide elongated surgical instruments or transmit suction or fluids. The present invention is not limited to a certain number of through channels 44, however, and may include one large channel or a number of smaller channels fitting within the lumen of the insertion tube 24.

A deflection control handle or lever 48, pivotally mounted on the control member 22, allows the surgeon to articulate the controllably bendable section 26 of the insertion tube 24. In the illustrated preferred embodiment, the lever 48 pivots from a neutral position, shown in FIG. 2, to a forward or rearward position, in the directions shown by arrow 50. The movement of the lever 48 causes a corresponding deflection of the controllably bendable section 26 of the insertion tube 24, whereby the amount of deflection is proportional to the amount of pivot of the lever. Thus, the full travel of the lever 48 in one direction will cause the controllably bendable section 26 at the distal end of the insertion tube 24 to form a maximum deflection angle with the longitudinal axis of the adjacent insertion tube. The movement of the lever 48 causes the controllably bendable section 26 to articulate in the same plane, as shown in phantom lines. Other arrangements in which the bendable section articulates in a plane perpendicular to the plane of movement of the lever 48, or other angular relationships, are possible. According to the principles of the present invention, the controllably bendable section 26 may articulate from a neutral position in one or two directions in only one plane. Of course, anatomical conduits in the human body are not only disposed in one plane, and the surgeon may access such circuitous channels by simply twisting the entire endoscopic system 20 to reorient the bending plane.

The insertion tube 24 generally comprises an elongated hollow flexible member having a typical length which may extend up to 250 centimeters. Preferably, the insertion tube 24 is constructed of a composite material co-extrusion (not shown) with an inner stiff tube and an outer elastic tube. The stiff inner tube may be manufactured from materials such as PET, unplasticized PVC or polyimide and provides torsional rigidity as well as a measure of hoop strength to the insertion tube 24. The outer flexible covering is commonly manufactured from an elastomer such as urethane, silicon, latex, etc. The principle aim in using a co-extrusion for the insertion tube 24 is to minimize the outside diameter and maximize the inner lumen diameter while providing adequate strength and flexibility for the particular surgical application. As an alternative, the co-extruded tube 24 may contain an embedded braid.

During a surgical procedure, the controllably bendable section 26 of the endoscope 20 inserts into an incision or natural port in the patient and the viewing tip 30 advances towards the target site. Any obstructions or turns in the anatomical channels are negotiated by manipulating the lever 48 on the control member 22 to cause the controllably bendable section 26 to articulate. As stated above, the control member 22 may also be twisted to rotate the bending plane of the controllably bendable section 26. The exact position of the viewing tip 30 is monitored by the surgeon through visual inspection via the fiber optics 28, or possibly by locating the radiopaque viewing tip with an x-ray machine. After finding the target site, the surgeon conducts the inspection or therapeutic action. The image of the target site is available through an eyepiece or, alternatively, the image may be transmitted to an auxiliary television monitor for more than one surgeon to observe. Surgical devices, irrigation fluids or aspirated materials may pass through the second inlet port 40 and through channels 44 and manipulated distally from the viewing tip 30 by well-known means.

Now referring to FIGS. 3–4, a control member housing 63 generally comprises a tubular gripping portion 64, a rear end cap 66, a lever support section 68 and a forward frustum shaped tip 70. Typically, an inner conduit 72 runs the length of the control member 22 for the fiber optic bundles 28 to pass and terminate in an optical fitting 73 at a proximal end of the end cap 66. The control member housing 63 is typically constructed of a rigid material and at least the gripping portion 64 may be covered with a knurled or rubber outer surface to enhance the hold of the surgeon. The upstanding lever 48 in the present embodiment, comprises two parallel legs 52a, 52b connected by an upper cross bar 54. The parallel legs 52 are pivotably mounted to a shaft 56 and are thus rotatably supported transversely through the lever support section 68. The lever 48 is keyed to the shaft 56 which, in turn, activates a steering control mechanism within the control member 22, as will be described below. The lever 48 may be fixed to the shaft 56 by any suitable means, such as threaded fasteners 58.

FIGS. 5 and 6a–c illustrate the steering control mechanism of the control member 22. A drive wheel 76, which includes two eccentrically positioned posts 78a, 78b, is mounted to the shaft 56. Two linkage arms 80a, 80b are pivotably mounted, one to each post 78, to the drive wheel 76. The proximal ends of each linkage arm 80a,b pivotably mount to upstanding posts 82a, 82b on a linkage plate 84. Fasteners, such as rivets or threaded nuts (not shown), secure the linkage arms 80a,b to both the drive wheel 76 and linkage plate 84. The linkage plate 84 pivots about a stationary axis 88, which mounts to the outer housing 63 of the control member. Two elongated cam slots 90a, 90b in the linkage plate 84 receive translation pins 92a, 92b attached to the inner surface of two parallel sliding actuation members 94a, 94b. The linkage arms 80 and linkage plate 84 pivot within a generally cylindrical space 95 created between the actuation members 94.

Figure 6C:
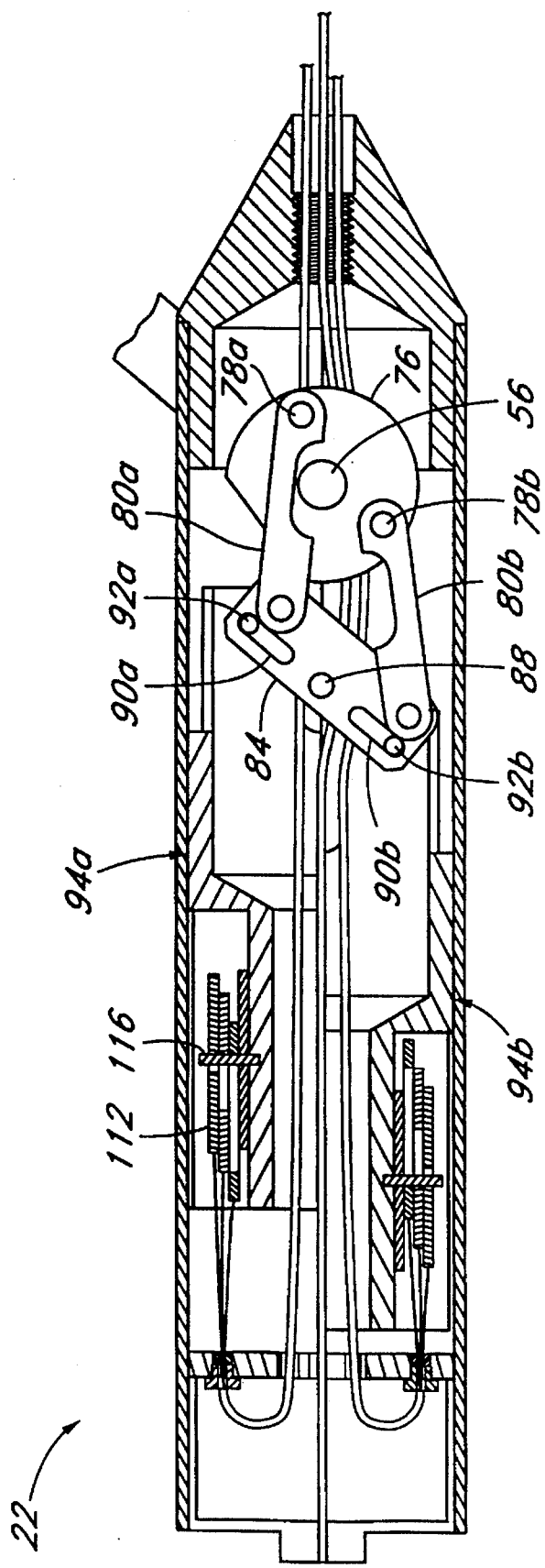

Referring more specifically to FIGS. 6b and 6c, rotary motion of the shaft 56 and associated drive wheel 76 is translated into linear motion of the actuation members 94a,b. From the neutral position shown in FIG. 6a, the wheel 76 may be rotated counter-clockwise (FIG. 6b) or clockwise (FIG. 6c) to cause the linkage arms 80a,b to be pulled or pushed generally along the longitudinal axis of the control member 22 due to the eccentric placement of the upstanding posts 78a,b. The linkage arms 80a,b, in turn, cause the linkage plate 84 to rotate about the stationary axis 88 so that the elongated slots 90a,b impart a camming force on the translation pins 92a,b which slide to the outside end of the slots due to the arc of rotation of the plate. The pins 92a,b and actuation members 94a,b thus slide in one longitudinal direction or another without binding with the elongated slots 90a,b.

As seen in FIGS. 5 and 6a, proximal end portions 96 of the actuation members 94a,b terminate a certain distance from a spacer 67 defining a clearance space 98, and have generally semi-circular cross-sections with inner flat sides 100 abutting one another. The actuation members 94a,b slidably mount within the control member housing 63 so as to freely translate longitudinally relative to the housing 63 and each other in means similar to a piston movement. Rotation of the shaft 56 causes linear translation of the actuation members 94 along the longitudinal axis of the control member 22 via the linkage arms 80 and linkage plate 84. As shown in FIG. 6a, oppositely facing semi-circular channels 102 in the flat sides 100 form a portion of the central throughbore 72 through which the fiber optic bundle 28 and endoscope pull cables 104 pass.

Figure 6D:
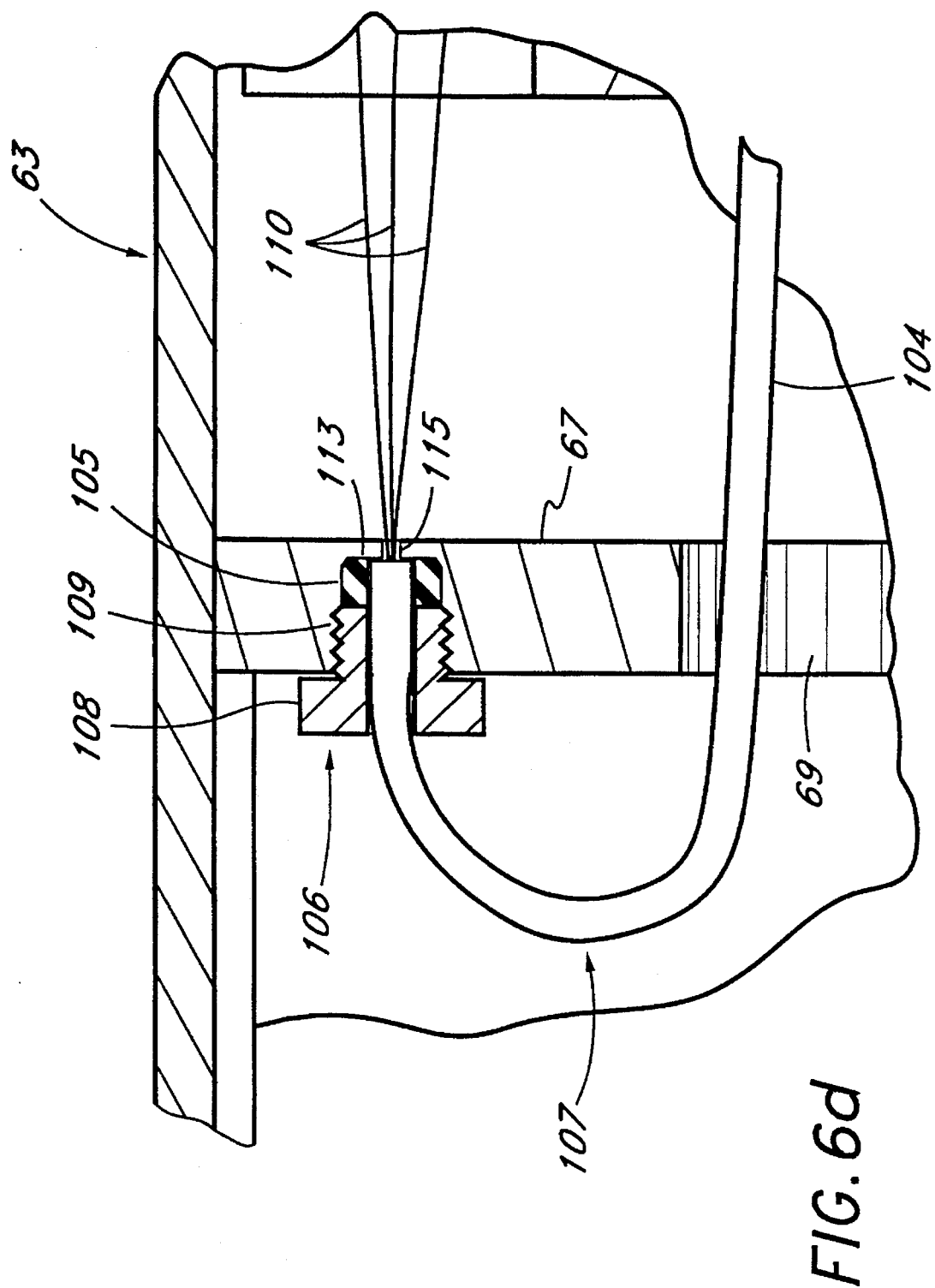

As seen best in FIG. 6d, the pull cables 104 travel through the actuation members 94a,b and thereafter through a central bore 69 in the spacer 67 before bending 180° around in loops 107 to terminate at swage fittings 106. Each swage fitting 106 generally comprises a threaded hollow nut 108 mating with a threaded recess 109 in the spacer 67. An elastomeric sleeve 105 closely surrounds the terminal end of the cable 104 within the recess 109 and is compressed by the nut 108 against a terminal wall 113 to firmly engage the cable without deformation thereto.

Steering operation wires 110 extend from the end of the cables 104 through a small aperture 115 in the terminal wall 113 and weld, braze or otherwise attach to the proximal end of series of differential pulling plates 112. The plates 112 slide longitudinally within generally rectangular receptacles 114 in the outer surface of both actuation members 94a,b and the wires 110 are recessed in shallow depressions 111 in the plates prior to brazing to eliminate material above the surface of the plates which might impede relative sliding motion. A movement pin or finger 116 extends outwardly from the inner surface of the receptacles 114 of each actuation member 94a,b through aligned slots 118 (FIGS. 7 and 8) in the differential pulling plates 112. Longitudinal movement of the actuation members 94 and attached movement fingers 116 transmits to the sliding plates 112 to pull or push the wires 110 relative to the termination of the cables 104 at the spacer 67.

Figure 12:
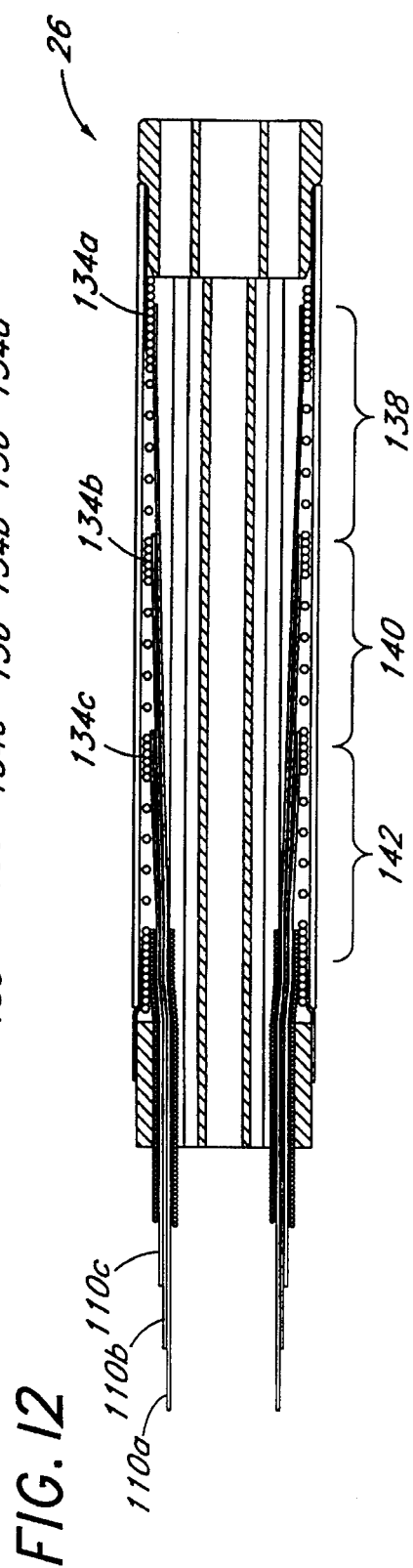
FIG. 12 is a cross-sectional view of the controllably bendable section of FIG. 9 showing the control wire attachment locations.

The pull wires 110 extend from the proximal end of the differential pulling plates 112 into the cables 104 which continue distally through the control member 22 and insertion tube 24 (FIG. 2) to terminate along the controllably bendable section 26. In the controllably bendable section 26, the steering control wires 110 emerge from the cables 104 and attach to the a coil spring 132 (as best seen in FIG. 12). Preferably, the control wires 110 are constructed of stainless steel and comprise flat ribbons having a thickness of approximately 0.002 inch thickness and a width of approximately 0.025 inch. By analysis, the cross-sectional area moment of inertia about the axis through the center of the narrow dimension is equal to 0.0064 the area moment of inertia about the axis through the center of the wide dimension. The control wires 110 of the present invention may have an area moment of inertia about an axis through the center of the narrow dimension less than or equal to 0.1 of the moment area of inertia about an axis through the center of the wide dimension. Furthermore, this ratio is preferably less than 0.01 and, most preferably, the control wires are dimensioned so that this ratio is approximately equal to 0.0064, as given by the above example. In the illustrated embodiment, there are three pull wires 110 for articulating the controllably bendable section 26 of the endoscope in opposing directions, for a total of six wires. The concepts embodied in the present invention, however, apply to control mechanisms utilizing more than one pull wire for each direction.

Figure 7:
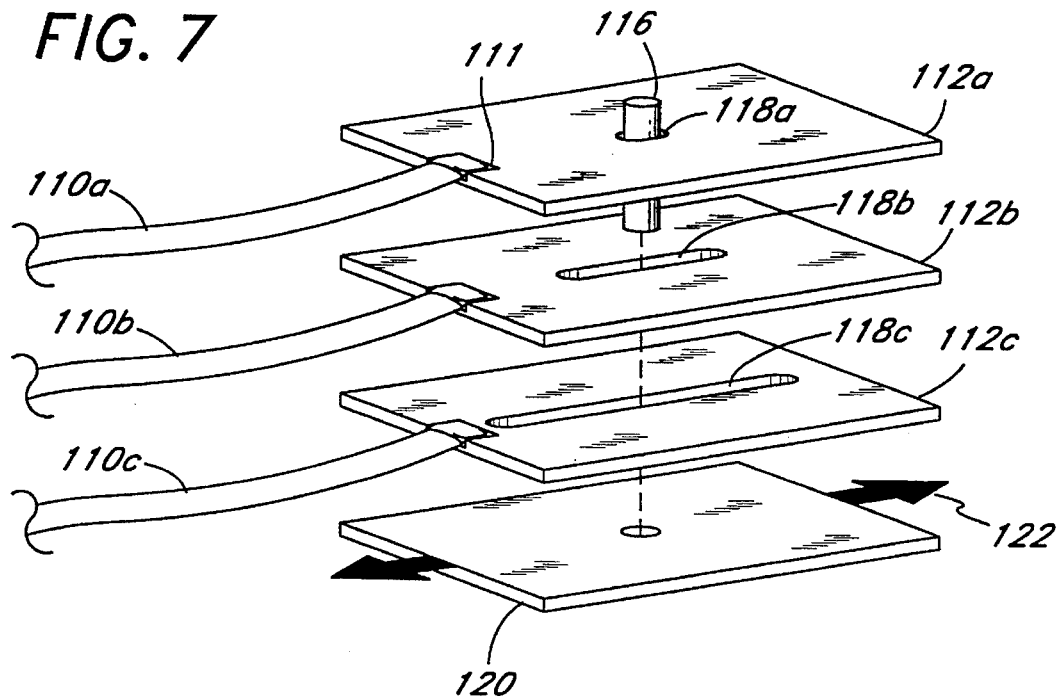
FIG. 7 is an exploded view of a portion of the control member of FIG. 6, showing the attachment of the proximal end of the operating wires to a series of sliding plates.
Figure 8:
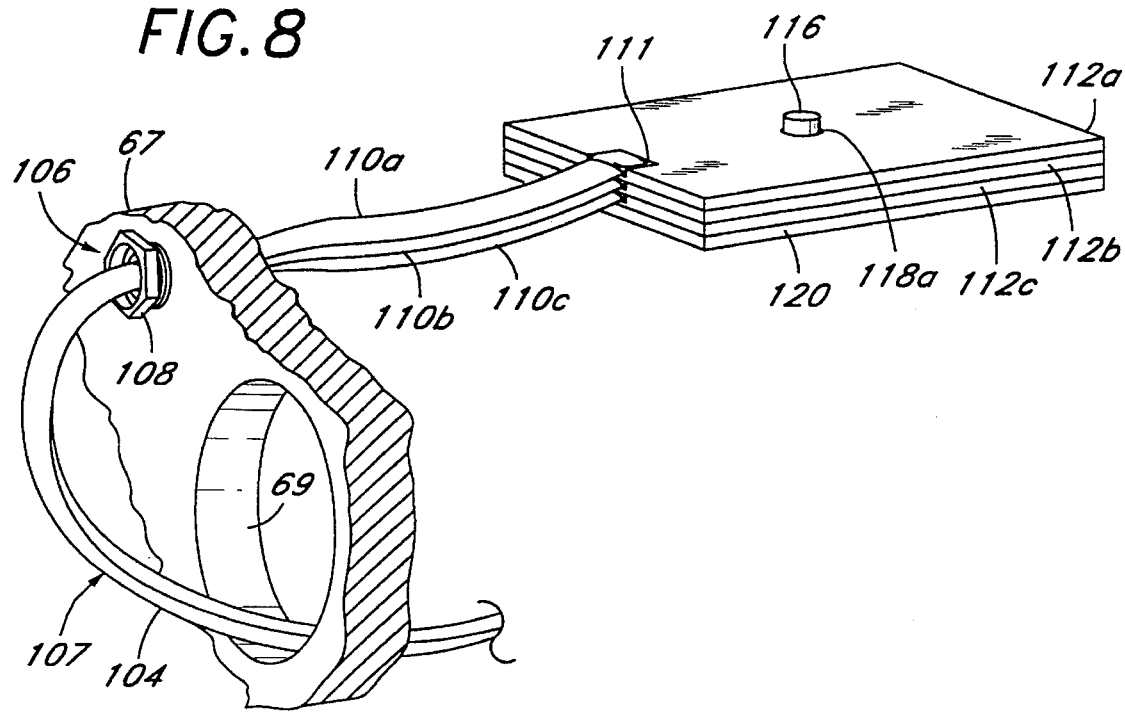
FIG. 8 is an assembled view of FIG. 7 showing the operating wires and sliding plates.

FIGS. 7 and 8, in conjunction with the cross-sectional views of FIG. 6, show the relative arrangement of the sliding plates 112. The particular detail shown relates to an upper assembly of sliding plates 112 and thus the fourth plate 120 shown at the bottom rigidly mounts to the upper actuation member 94a, or, alternatively, represents the actuation member itself. The movement finger 116 rigidly fixes to the upper member 94a via the upper plate 120 which therefore translates in the longitudinal directions shown. The finger 116 extends through a small slot 118a slightly longer than the finger diameter in the first sliding plate 112a. The finger 116 also extends through the second and third sliding plates 112b and 112c via their aligned slots 118b, 118c, respectively. The aligned slots 118 become progressively longer in the dimension parallel to the axis of the control member 22 from the first to the third plate 112. Thus, when the movement finger 116 translates in the direction of the arrow 122 as shown, the first sliding plate 112a and attached pull wire 110a travel the same distance as does the sliding member 120. The second sliding plate 112b, nominally restrained by an attached pull wire 110b, will be held from translating in the direction of the first sliding plate 112a until the finger 116 contacts one of the rounded edges of the slot 118b, whereupon the second plate will move. Eventually, as the sliding member 120 continues to move, the movement finger 116 contacts one of the rounded edges of the slot 118c in the third plate 112c and causes the third plate and attached ribbon or pull wire 110c to move as well.

In the configuration shown in FIG. 6c, the shaft 56 has been rotated in a clockwise direction so that the upper sliding member 94a translates toward the distal end of the control member 22 to the right and moves the differential sliding plates 112 in the same direction. The resulting position of the sliding plates 112 is as shown, with the distal end of the first plate 112a being slightly more aligned with the sliding member 120 than the second plate 112b which, in turn, is positioned to the right of the third plate 112c. This differential movement causes the pull wires 110 to move relative to each other in a corresponding manner. Since the embodiment of FIG. 1 shows the controllably bendable section 26 capable of articulating in the plane vertically through the control lever 48, FIG. 6c, with the control mechanism pulling the upper wires, shows a configuration whereby the bendable section is deflected upward. Each wire attaches to different locations along the bendable section, and the relative distance travelled by the pull wires directly affects the amount and shape of bend, as will be more fully described below.

The above discussion describes the means for articulating the controllably bendable section 26 by pulling one set of wires 110. As illustrated in the figures, the second set of wires 110 will be actuated in the opposing direction, or pushed toward the controllably bendable section 26. For infinitely stiff wires this would enhance the pulling operation of the first set of wires by applying a second additive bending moment. However, the size and shape of the preferred wires reduces their individual column strengths to below that required to sustain a compression force capable of bending the section 26. The opposing movement of the second set of wires does assist the deflection process by providing slack, or feeding wire to the controllably bendable section 26 on the outer side of the bend. Without this feeding capacity, the second set of wires would be a hindrance to free articulation. Furthermore, as will be more fully described below in conjunction with FIGS. 11 and 12, feeding of wire 110 from the opposite side helps prevent the coil spring 132, to which the wires attach within the controllably bendable section 26, from being compressed along its length.

The particular embodiment of differentially pulling the wires, as shown in FIGS. 6–8, represents only one means to cause differential pulling. In the preferred embodiment, the pull wires 110 are activated at different times, or sequentially. Other mechanisms for causing sequential pulling of the wires are within the scope of the invention. Alternatively, the wires may be pulled all at the same time but at different rates, such as by wrapping the proximal ends of the pull wires around actuation shafts of different diameters.

The pull wires 110 displace relative to an outer sheath 124 of the cables 104 which contains the pull wires. The sheath 124 firmly attaches at the distal end to the coil spring 132 and at the proximal end is held firmly by the swage fitting 106. Actuating the sliding plates 112 thus displaces the wires 110 within the sheath 124 to transmit axial motion to the controllably bendable section 26 relative to the distal end of the sheath 124. Advantageously, a 0.0001 inch Teflon coating on the wires 110 reduces sliding friction with the sheath 124. The sheath-enclosed wire 110 arrangement allows linear motion of the sliding plates to be precisely transmitted to the wires at the controllably bendable section 26 regardless of the bends formed in the insertion tube 24, in a similar manner as is well known in bicycle control cables.

As shown in FIGS. 9 and 10a, the cable sheaths 124 for containing the operating wires 110 preferably comprise oval-shaped wire coils 126 which surround the wires and constrain them along the length of the insertion tube 24. FIG. 10a illustrates the internal components of one embodiment of the insertion tube 24, from the control member 22 to the controllably bendable section 26. The components extend in a loose alignment through the tube to enable relative longitudinal motion. Advantageously, the close enclosure of the control wires 110 by the sheath 124 maximizes the inner lumen space within the insertion tube 24 for the locating light fibers 38 and through channels 44. The minimized radial projection of the sheath 124 within the insertion tube 24 allows a second fiber optic bundle (not shown), or more through channels 44 to be utilized by the surgeon, which is highly beneficial in endoscopic surgical applications having small insertion tube diameter limits.

Each oval-shaped coil wire 126 is tightly wound to provide sufficient axial column strength. The coil provides enhanced bending flexibility facilitating smooth insertion and retraction into circuitous anatomical channels. Alternatively, the cable sheath 124 may be constructed of a solid thin-walled metallic tube which is deformed into the oval shape.

In a preferred manufacturing procedure, the sheath coil wire 126 is tightly wrapped around an oval shaped mandrel (not shown). The coil wire 126 is preferably a memory-shaped alloy such as a nickel-titanium alloy, which is preferred because internal strains may be removed by heat treating. Such heat treatment eliminates the internal stresses associated with coiling around the mandrel, as heat at a certain temperature and for a certain time relaxes intercrystalline forces, as is well known in the art. In the absence of heat treating, oval-wrapped coils tend to produce a secondary spiral when the oval mandrel is removed.

Figure 11:
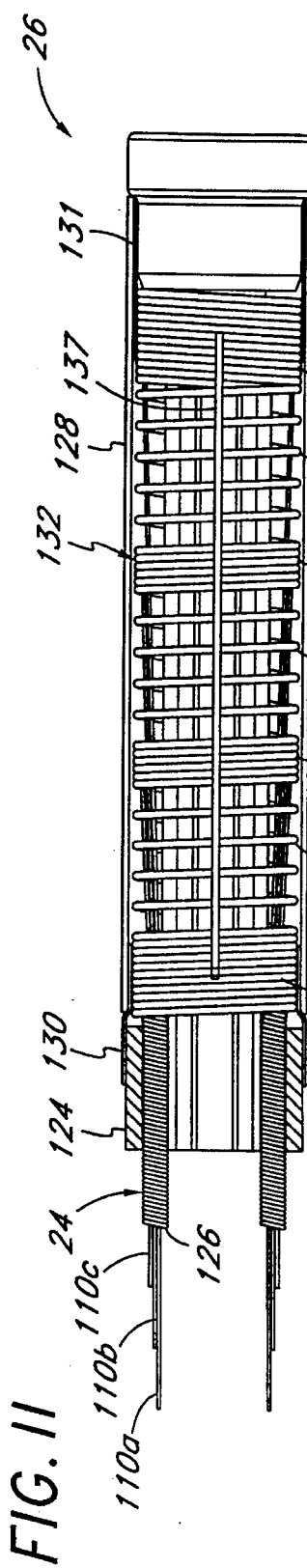
FIG. 11 is a partial longitudinal cross-sectional view of the controllably bendable section of FIG. 9.

Referring now to FIGS. 9 and 11, the controllably bendable section 26 includes an outer covering 128 terminating in the generally cylindrical viewing tip 30. The outer covering 128 preferably is constructed of a thin elastomeric material for maximum flexibility. At the proximal end of the controllably bendable section 26, a stainless steel coupling sleeve 130 extends between the outer covering 128 and the coil spring 132 and thereafter bonds to the outer co-extrusion of the insertion tube 24. The coupling sleeve 130 may be glued, soldered, brazed or epoxied to the coil spring 132, and glued or epoxied to the covering 128 and outside of the tube 24. A second stainless steel coupling sleeve 131 (FIG. 11) extends between the outer covering 128 and the distal end of the coil spring 132 and thereafter around a reduced portion of the viewing tip 30. The sleeve 131 may be glued, soldered, brazed or epoxied to the coil spring 132 and viewing tip 30, and glued or epoxied to the outer cover 128. The resulting assembly comprises a chamber within the outer cover 128 wherein the coil spring 132 attaches at both ends yet is free to move axially inbetween.

Referring to FIGS. 10a–d, the internal components of the endoscope 20, such as the fiber optic bundle 28, light fibers 38 and through channels 44, lie symmetrically about a neutral bending plane, in this case, a horizontal plane as the pull wires 110 are attached at top and bottom. In practice, the components may not actually be symmetric about the bending plane but distributed so as to create a symmetric area moment of inertia about the bending plane. The arrangement of the components within the controllably bendable section 26 in this manner results in symmetric bending resistance and thus an equivalent application of stress to the pull wires 110 when bending in either direction. In addition, it is beneficial to arrange the components so that the area moment of inertia is symmetric about the plane normal to the plane of bending, in this case, the vertical plane, as this ensures bending is generally confined to one plane and no twisting will take place.

in the preferred embodiment, there are three working channels 44, two with an outside diameter 0.020 and an inside diameter of 0.018 inch, and one with an outside diameter of 0.055 and an inside diameter of 0.047 inch. In this embodiment, there are six illumination fibers 38 each having a 0.010 inch outside diameter. The fiber optic bundle 28 has an outside diameter of 0.024 inch including a surrounding jacket. The insertion tube 24 has an outside diameter of between 0.116 and 0.118 inches and an inner lumen diameter of between 0.095 and 0.097 inches. In other embodiments having only the fiber optic bundle 28, the outside diameter of the insertion tube 24 may reduced to as low as 0.080 inch.

Referring to FIGS. 10e, the distal face of the viewing tip 30 is shown. The terminal arrangement of the light fibers 38 changes slightly from that within the insertion tube 24, in that the light fibers are grouped into two bundles of three and placed on both sides of the microlens 28a, which terminates the fiber optic bundle 28, for best illumination of the target site.

In an alternative embodiment, only one set of pull wires 110 can be used when a particularly large fiber optic bundle 28 or through channel 44 is required for certain applications. In this instance, the overly stiff element must be placed as far away from the point of connection of the pull wires 110 as possible to maximize the moment arm in order to successfully cause bending. Thus, there will only be one set of pull wires 110 on one side of the insertion tube with the stiff element on the opposite side and the controllably bendable section 26 will therefore be capable of deflection in only one direction. Preferably, at least one axial spine must be attached along the length of the coil spring 32 in the neutral bending plane to prevent the spring from compressing on the side opposite the stiff element when the wires are pulled.

The preferred endoscope of the present invention utilizes a 0.6 mm outside diameter fused silica coherent fiber optic bundle 28, including a jacket covering, having a limit of bend radius of 30 mm set by the manufacturer, in this case, Sumitomo or Fujikura. The bundles typically comprises 10,000 individual fibers. The present embodiment contemplates a 2.8 mm outside diameter insertion tube 24 with a deflection system capable of producing a 90° bend with less than a 50 mm average radius of curvature, and more preferably a 30 mm bend radius, without exceeding the tensile yield strength of the pull wires 110.

Referring to FIGS. 10–12, and to the internal components of the controllably bendable section 26 in greater detail, the sheath 124 around the pull wires 110 extends into the proximal end of the bendable section and attaches to a proximal end 133 of the variable pitch coil spring 132. The sheath 124 is preferably soldered, brazed or welded to the inner wall of the coil spring 132. In one embodiment, in which the sheath 124 is nickel-titanium, the sheath receives a gold plating on the distal end to facilitate attachment to the coil spring 132. As is known in the art, nickel-titanium alloys are difficult to braze, and thus the gold plating is added to provide an area to adhere the braze material.

The coil spring 132 spans the length of the controllably bendable section 26 adjacent or in contact with the inner surface of the elastomeric cover 128. The spring 132 comprises the proximal tightly wound length 133 and alternating lengths of tightly and loosely wound lengths of coil 134 and 136, respectively. Each of the pull wires 110 welds or brazes to a tightly wound section 134 of the coil spring 132.

In one preferred embodiment, the coil spring 132 is fabricated from 0.005 inch thick spring tempered stainless steel wire wound into a coil with an outer diameter of 0.107 inches. The coil spring is stretched to leave gaps of 0.010 to 0.015 inches between adjacent loops.

As illustrated in FIG. 12, the innermost pull wire 110a mounts to the inner surface of a distal tightly wound section 134a of the coil spring. In a similar manner, the second pull wire 110b mounts to a second tightly would section 134b of the coil spring. And finally, the outermost pull wire 110c on each side mounts to a proximal tightly wound section 134c of the coil spring. Each of the pull wires 110 thus may apply a bending moment to the controllably bendable section 26 at different locations. The pull wires attach to the inner surface of the coil spring 132 so that they have the same moment arm with respect to the longitudinal axis of the controllably bendable section 26. This allows each of the pull wires 110 to apply an equivalent moment to the controllably bendable section 26. The wires 110 may alternatively pass through two loosely wound coils and attach to the outside surface of the tightly wound regions 134 to simplify assembly.

Ideally, the reverse feeding of the control wire 110 on the diametrically opposite side from a pulling wire provides an axial force sufficient to maintain the spacing between the tightly wound sections 134 along the neutral axis. Lack of such axial support results in the wire displacement compressing the coil spring 132 rather than applying a bending moment. In one preferred embodiment, two axially disposed spines 137 attach to the tightly wound section on both sides of the spring along the neutral axis. Such spines 137 prevent compression of the coil spring 132 while adding negligible bending stiffness due to their position along the neutral axis. In an alternative arrangement, spacers may replace the spines 137 between the tightly wound regions 134.

Figure 13:
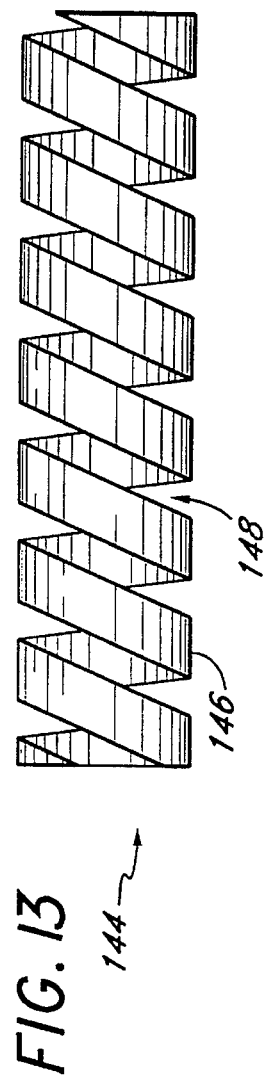
FIG. 13 is a side elevational view of an alternative flexible member used in the controllably bendable section of FIG. 11.

In an alternative embodiment, shown in FIG. 13, a coiled ribbon 144 replaces the coil spring 132 in the controllably bendable section 26. The coiled ribbon 144 possesses an increased axial stiffness as compared to the coil spring 132 and thus may withstand axial compressive forces generated by the pulling wires 110 without a spine The coiled ribbon 144 possesses low stiffness in bending and sufficient hoop strength. Furthermore, the coiled ribbon 144 presents an evenly spaced series of solid portions 146 separated by gaps 148, allowing a large selection of attachment locations for the control wires 110. In one preferred embodiment, the coiled ribbon 144 is constructed of spring tempered stainless steel ribbon having a thicknesss of 0.004 inch and a width of 0.040 inch. The coil ribbon is prestretched to form axial gaps of 0.025 inches between adjacent loops.

A still further embodiment (not shown) for a coil spring 132 replacement, comprises aligned and hingedly connected vertebrae as is well-known in the art. In this configuration, the pull wires 110 attach in a similar manner as above to one of the vertebrae at a location axially equivalent to the location of the tightly wound coil spring sections 134.

In a preferred situation, with reference to FIGS. 8 and 12, the pull wires 110 are actuated with the differentially pulling plates 112 of the control member 22 and apply a bending moment sequentially. The controllably bendable section 26 thus may be divided into three discrete regions capable of deflection with respect to each other. A distal tip region 138 extends from the middle tightly wound coil 134b to the distal tightly wound section 134a. The innermost pull wire 110a may be attached to the first sliding plate 112a as described in conjunction with FIGS. 7 and 8, so that the distal region 138 of the controllably bendable section 26 is articulated first to a certain degree. Thereafter, the second pull wire 110b, attached to the second sliding plate 112b, will be pulled after the actuation finger 116 has translated a certain distance to contact the inner rim of the enlarged slot 118b in the second plate. The distance travelled by the actuation finger 116 prior to contacting the second enlarged slot 118b, and moving the second plate 112b, is approximately equivalent to half the span of the aperture along the direction of finger motion. The extreme distal region 138 of the controllably bendable section, therefore, comprises the only section to initially articulate due to the moment applied by the first pull wire 110a.

Further rotation of the shaft 56 causes the actuation finger 116 to contact the second enlarged slot 118b in the second plate 112b, causing a middle region 140 of the controllably bendable section to commence articulation. The middle region 140 extends from the proximal tightly wound coil section 134c to the middle tightly wound section 134b. The total angle of deflection at the viewing tip 30 is now the sum of the amount the distal 138 and middle 140 regions deflect.

Subsequent to the deflection of the middle region 140, and commencing when the actuation finger 116 contacts the edge of the enlarged slot 118c in the third plate 112c, the third pull wire 110c causes a proximal region 142 to deflect. The amount of deflection of the viewing tip 30 is thus the combined sum of deflection of the three regions of the controllably bendable section.

In the particular embodiment illustrated, the pull wires 110 connect to the controllably bendable section 26 and are actuated in such a manner as to articulate the extreme distal region 138 of the endoscope first and subsequently articulate two other regions 140, 142 proximal to the distal region. The shape of the controllably bendable section 26 while undergoing articulation will thus reflect the particular sequence the pull wires 110 are actuated. However, the sequence of pulling, and corresponding shape of the controllably bendable section 26, need not be limited to the embodiment shown. The provision of multiple pull wires 110 reduces the stress associated with each wire for a certain deflection angle and may be accomplished regardless of the pulling sequence. For instance, the wire 110a attached farthest distally may be actuated last and thus the distal region 138 will remain generally aligned with the middle region if only the second two wires 110b and 110c are pulled. Any number of combinations with respect to the order the wires 110 are pulled are possible.

Furthermore, the relative lag between the actuation of one wire and the next in sequence may be altered. In FIG. 8, the actuation finger 116 extends through the differentially sized aligned holes 118 which cause the plates 112 to sequentially move when the finger translates. The width of each hole 118 determines exactly when that particular plate is actuated. To delay the movement of a plate 112, the corresponding hole 118 may be widened. To cause the plate to commence movement sooner, the hole may be narrowed. The embodiment shown, in which the holes 118 increase generally linearly in size represents a preferred embodiment and should not be construed as exclusive or limiting.

Advantageously, the flat configuration of the pull wires provides equivalent strength but far greater flexibility in the bending plane than would round pull wires having equivalent cross-sectional area. A flat wire having the preferred ratio of thickness to width as stated above possesses an area moment of inertia about the bending axis which is less than 1/10 that of a round wire of equivalent cross-sectional area. Furthermore, combining two or more flat wires capable of sliding relative to each other contributes minimal extra resistance to bending above that of the stiffness of the independent wires themselves. Two flat wires, for example, having the preferred ratio of thickness to width as stated above possess a combined area moment of inertia about the bending axis which is less than 1/20 that of a round wire of equivalent cross-sectional area. In short, adding cross-sectional material equally to round and multiple flat wires increases the axial pulling capacity at the same rate but the increase in stiffness of the multiple wires is lower than that of a larger round wire. Therefore, with the flat side of the pull wires 110 disposed perpendicular to the bending plane of the endoscope, there is a minimized stiffness added to the controllably bendable section 26 of the insertion tube 24 by the pull wires themselves.

Consequently, a predetermined deflection of the viewing tip 30 with respect to the longitudinal axis of the insertion tube 24 may be attained with a reduced amount of stress in each wire 110 as compared to a conventional configuration utilizing only one round wire. Endoscopes incorporating the present invention may be made smaller and deflect farther than conventional devices due to the sharing of stress between the wires. In the preferred embodiment, the endoscope has a maximum insertion tube outer diameter of 2.8 mm and may repeatedly bend 90 degrees in opposing directions without overly stressing the pull wires 110. A detailed mechanical analysis of tube bending is provided below.

General Tube Deflection Analysis

The following is a generalized description of the mechanics involved in the deflection or bending of the distal end of a tubular device in which the deflection or bending of the deflectable portion is actuated by an internally located and axially directed cable system. The equations governing the deflection of the tubular device are developed in order to set the stage for a new concept in actuating the deflection of the distal ends of endoscopes and catheter type devices.

It is assumed that the tubular device is constructed of truly elastic material. It is further assumed that any components encased within the tubular device are also truly elastic and are axially arranged within the device and symmetrically positioned with respect to the central and neutral axis of the device. Also, it is assumed that during bending the elastic limit of any component contained within or contributing to the structure of the tubular device is never exceeded.

Deflection of the tubular device is actuated by a moment generated by an axial tensile or compressive force eccentrically applied parallel to the axis of the tubular device. Since the force actuator (a cable or wire) moves with respect to the tubular device and since this same actuator generates a force which is always parallel to the axis of the tubular device, it is assumed that the resultant bending moment is constant and no small deflection restrictions are required in the theoretical presentation.

Figure 14:
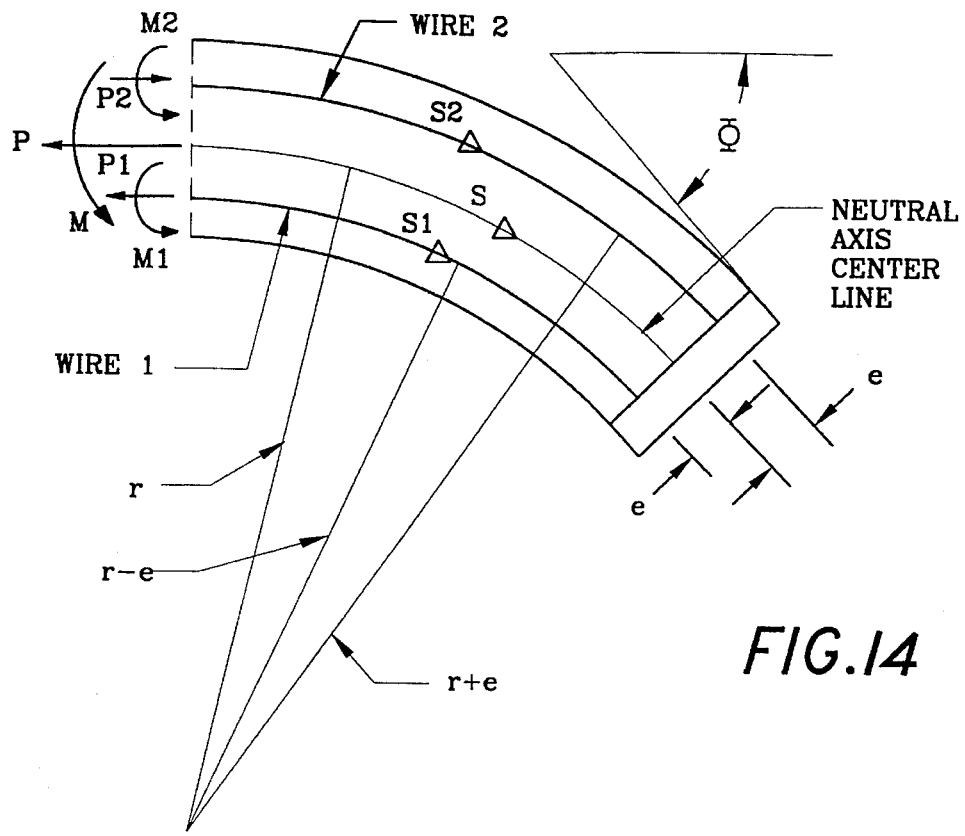
FIG. 14 is a force/moment diagram of a simple tube section in bending.

FIG. 14 illustrates in generalized form the mechanics involved in the deflection of most mechanically actuated endoscopes and catheters. In this configuration, two actuating cables (wire 1 and wire 2) are presented (wire 2 can be removed without any loss to the generalized model). Only the deflectable distal portion of the tubular device is illustrated. Deflection of the deflectable portion through an angle $\Phi$ is realized by the simultaneous push ($P_2$ compressive force) of wire 2 and pull ($P_1$ tensile force) of wire 1. Since the wires are positioned a radial distance "e" from the tubular axis, a bending moment ($M = P_1 e + P_2 e$) is generated which acts to bend the deflectable portion of the tubular device. This deflection process involves the bending of the tubular element (or movement of articulated disks or vertebrae), the bending of all encased elements and the flexure of wire 1 and wire 2.

Referring to FIG. 14, $P_1$ is the tensile or pulling load transmitted along wire 1, $M_1$ is resulting moment acting on wire 1, and, $S_1$ is an incremental length taken along wire 1. The subscript 2 refers to corresponding variables describing the pushing or compressive force transmitted along wire 2. M and P are the resultant axial force and moment respectively acting on the deflectable portion as a result of $P_1$ and $P_2$. S is an incremental length taken along the neutral axis and e is the radial distance from the neutral axis for the applied forces $P_1$ and $P_2$. The bending radius of the neutral or central axis is r, while r−e and r+e represented the bend radius of wires 1 and 2 respectively. Summing all axially directed forces gives $$P - P_1 - P_2 = 0 \tag{1}$$

Summing all radial forces gives (not shown in FIG. 14)

$$Q + Q_1 + Q_2 = 0 \tag{2}$$

And summation of moments gives $$M + M_1 + M_2 = P_1 e + P_2 e \tag{3}$$

Defining the rate of change of the moments along the wire with the following relations $$Q = \frac{d}{dS} M \quad Q_1 = \frac{d}{dS_1} M_1 \quad Q_2 = \frac{d}{dS_2} M_2 \tag{4}$$

and $$M = \sum_i E_i I_i \frac{d\Phi}{dS} \quad M_1 = E_s I_s \frac{d\Phi}{dS_1} \quad M_2 = E_s I_s \frac{d\Phi}{dS_2} \tag{5}$$

where $E_i$ and $I_i$ represent the modulus of elasticity and the inertia respectively of the ith element (e.g. fiber bundle, working channel tube, tubular sheath, etc) encased within the tubular structure and $E_s$ and $I_s$ represent the modulus and inertia respectively of the activation wires. It is assumed that wire 1 and wire 2 have the same properties and dimensions. The real solution requires that the radius of curvature for the deflected portion of the catheter is constant ($dr/d\Phi=0$). Using the fact that, $$\frac{d\Phi}{dS} = \frac{1}{r} \quad \frac{d\Phi}{dS_1} = \frac{1}{(r-e)} \quad \frac{d\Phi}{dS_2} = \frac{1}{(r+e)} \quad (6)$$

after several intermediate steps and since the radial distance e is much smaller than the bend radius of the tubular device, we can use the following relationship, $$\frac{1}{r} = \frac{d\Phi}{dS} \quad (7)$$

and rearrange terms to get the relationship between the total angle of deflection and the loading forces, or $$\frac{d\Phi}{dS} = \frac{(P_1+P_2)e}{\sum_i E_i I_i + 2E_s I_s} \quad (8)$$

Integrating over the total length L of the deflectable portion of the tubular device gives the deflection angle as a function of the loading forces.

$$\Phi = \frac{(P_1+P_2)eL}{\sum_i E_i I_i + 2E_s I_s} \quad (9)$$

Equation (9) describes the relationship between the deflection angle and the force required to attain the desired angle for most mechanically actuated deflecting catheters and endoscopes. As can be seen, there is a linear relationship between $\Phi$ and loads $P_1$ and $P_2$. In practice the contribution of $P_2$ (or the push forced) is insignificant in comparison to $P_1$ since the maximum effective magnitude of $P_2$ is below $$P_2(max) = \frac{\pi^2 E_s I_s}{L^2} \quad (10)$$

or Euler's critical load for neutral instability (i.e., buckling). Although the contribution of wire 2 to the deflection may be small, its contribution toward the recovery from a deflection bend may be significant.

The achievement of adequate deflection while minimizing axial load has been actively pursued by numerous designers. Much of the attention in these efforts has been directed toward reducing the contribution of the denominator in equation (9), as with the development of highly elastic polymers, the adoption of unique tubular geometric profiles (e.g., notched tubes, etc.) and the replacement of deformable (i.e., elastic) materials with articulating disks or vertebrae. However, a practical limit is reached whereby the only way to insured that the wires do not fail is to reduced the angle of deflection.

Multiple Control Wire Analysis

These problems along with the demand for smaller deflectable endoscopes and catheters has inspired the herein proposed concept of maximizing angular deflection by not only minimizing the rigidity of the tubular device as represented in the EI values (E being the Modulus of Elasticity, I the Area Moment of Inertia), but by also distributing the applied loads. As will be shown, by applying multiple loads to sequential or various segments of the deflectable portion of the tubular device, one can effect efficient deflection angles while minimizing the load on any single load carrying wire. In addition, the placement and activation of loads (and subsequent moments) in predetermined sequences allows for actual shaping of the curve taken by the deflectable portion of the endoscope or catheter.

Referring again to equation (9) and accepting the assumptions presented above, it becomes evident that the method of loading and the resultant deflection angle are additive. If we treat FIG. 14 as one segment of a multi-segment deflectable device, each with its own means of loading (i.e. wires), then the total deflection angle obtainable would be a linear combination of the deflection angles of the individual segments. For example, lets us suppose, as displayed in FIG. 15, that a deflectable portion of a tubular device is divided into three segments and each segment is provided with a means for actuating a moment. While we will use an example with three segments the argument presented can be generalized to the case where the deflectable portion of a tubular device is subdivided into a plurality of segments.

Figure 15:
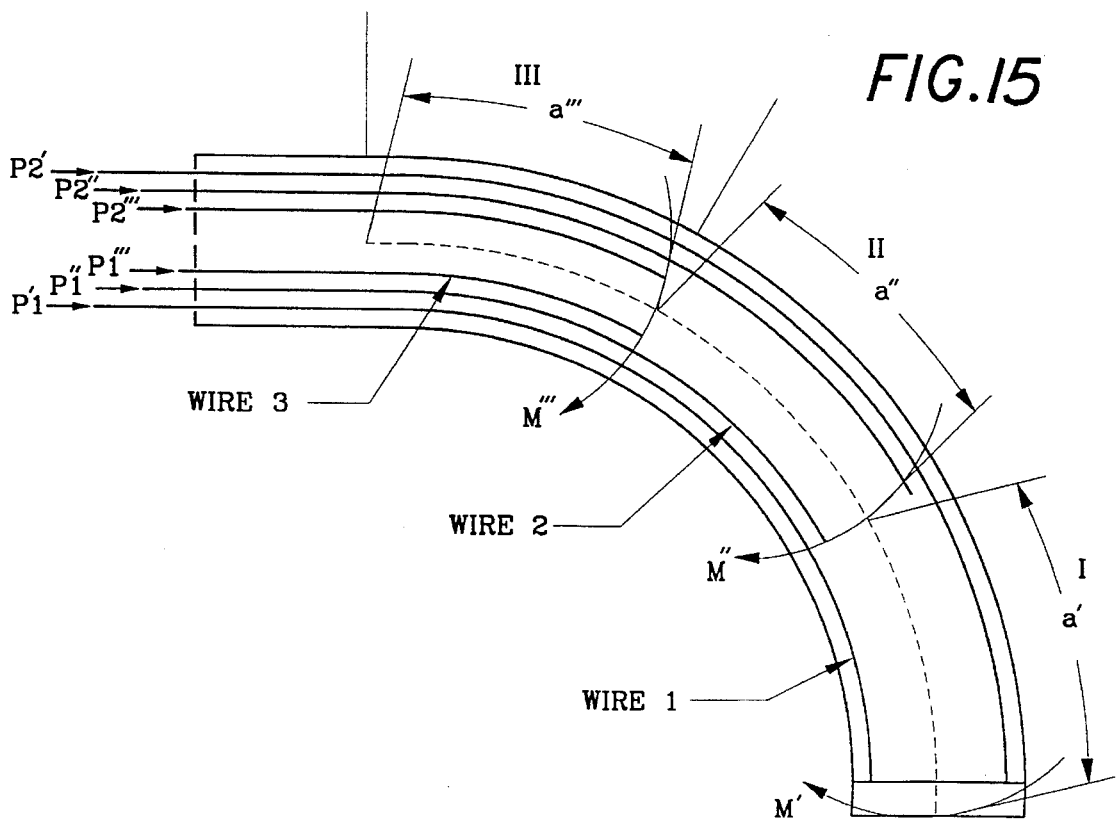
FIG. 15 is a force/moment diagram of a tube section subjected to bending by three wires.

FIG. 15 illustrates the deflectable portion of a tubular device which has been divide in three sections I, II and III with lengths $a^j$ (j=I, II or III). Each segment has its own moment $M^j$ created by the application of loads $P_1^j$ and $P_2^j$ along wires 1, 2 or 3 corresponding to segments I, II and III respectively. All discussions of wires actually refers to wire pairs with one wire providing a pull or tensile load and the other providing a push or compressive load. It is assumed that all wires are aligned along the bending plane and, when loaded, generate moments which also act on along this same plane.

In this multi-moment scheme, the total deflection angle $\Phi$ is determined from the summation of deflection angles generated by the action of the moments on each segment of the deflectable portion of the tube. Or $$\Phi = \Phi_1 + \Phi_2 + \Phi_3 \quad (11)$$

where $\Phi_1$ is the angle created by the action of $M^I$ on segments I, II and III, $\Phi_2$ is the angle generated by the action of $M^{II}$ on segments II and III and $\Phi_3$ is angle generated by the action of $M^{III}$ on segment III. Each of these deflection angles ($\Phi_1$, $\Phi_2$ and $\Phi_3$) can further be subdivided into even smaller angles resulting from the action of any single load on a particular segment such that $$\begin{aligned}\Phi_1 &= \Phi_{11} + \Phi_{12} + \Phi_{13}\\ \Phi_2 &= \Phi_{21} + \Phi_{22}\\ \Phi_3 &= \Phi_{31}\end{aligned} \quad (12)$$

where from (9) these angles are described by $$\Phi_{11} = \frac{1}{\sum_i E_i I_i + 6E_s I_s} a^{III} (P_1^I + P_2^I) e^I \quad (13)$$

$$\Phi_{12} = \frac{1}{\sum_i E_i I_i + 4E_s I_s} a^{II} (P_1^I + P_2^I) e^I$$

$$\Phi_{13} = \frac{1}{\sum_i E_i I_i + 2E_s I_s} a^I (P_1^I + P_2^I) e^I$$

$$\Phi_{21} = \frac{1}{\sum_i E_i I_i + 6E_s I_s} a^{III} (P_1^{II} + P_2^{II}) e^{II}$$

$$\Phi_{22} = \frac{1}{\sum_i E_i I_i + 4E_s I_s} a^{II} (P_1^{II} + P_2^{II}) e^{II}$$

$$\Phi_{31} = \frac{1}{\sum_i E_i I_i + 6E_s I_s} a^{III} (P_1^{III} + P_2^{III}) e^{III}$$

Equations (13) utilize generalized variables $a^j$, $e^j$, $P_1^j$ and $P_2^j$ (j=I, II or III) in place of L, e and the loads in equation (9).

Also in (13) a factor of 2, 4 or 6 is seen multiplying the term $E_s I_s$. These factors arise from the number of wires present within any given segment. During deflection these wires must also be bent.

The application of loads $P_1^j$ and $P_2^i$ (j=I, II and III) result in developed moments $M^j$. These moments, when applied, result in a different bending radius for each segment described by $$r^I = \frac{\sum_i E_i I_i + 2E_s I_s}{M^I} \quad (14)$$

$$r^{II} = \frac{\sum_i E_i I_i + 4E_s I_s}{M^{II} + M^I}$$

$$r^{III} = \frac{\sum_i E_i I_i + 6E_s I_s}{M^{III} + M^{II} + M^I}$$

Though each segment of the deflectable portion of the tube has its own radius, the bend radius corresponding to each segment is constant over that segment ($dr/d\Phi = 0$ for each individual segment).

It is evident that, theoretically, numerous bend radii (shapes) and deflection angles can be generated by changing segment lengths ($a^j$), loads P and radial placement of loads e.

To illustrate, assume the following relations:

$$a^I = a^{II} = a^{III} = \frac{L}{3} \quad (15)$$

$$P_1^I = P_1^{II} = P_1^{III} = P_1$$

$$P_2^I = P_2^{II} = P_2^{III} = P_2$$

$$e^I = e^{II} = e^{III} = e$$

$$P_2 << P_1$$

$$\Phi_{11} = \frac{L}{3} \frac{P_1 e}{\sum_i E_i I_i + 6E_s I_s} \quad (16)$$

$$\Phi_{12} = \frac{L}{3} \frac{P_1 e}{\sum_i E_i I_i + 4E_s I_s}$$

$$\Phi_{13} = \frac{L}{3} \frac{P_1 e}{\sum_i E_i I_i + 2E_s I_s}$$

$$\Phi_{21} = \frac{L}{3} \frac{P_1 e}{\sum_i E_i I_i + 6E_s I_s}$$

$$\Phi_{22} = \frac{L}{3} \frac{P_1 e}{\sum_i E_i I_i + 4E_s I_s}$$

$$\Phi_{31} = \frac{L}{3} \frac{P_1 e}{\sum_i E_i I_i + 6E_s I_s}$$

Adoption of these assumptions simplifies equations (13) to Equations (16) and illustrates the angular contribution of each moment $M^j$ acting on each segment j to the total deflection angle $\Phi$. By choosing which moments (or loads) to actuate, different bend shapes and deflection angles can be generated. An examination of several cases will illustrate this.

EXAMPLE 1—all moments (loads) actuated.

With all moments actuated, the total deflection angle $\Phi$ is described by equations (11) and (12). By incorporating (16) into (12) and then (11) we get $$\Phi = \frac{L}{3} Pe \left( \frac{3}{\sum_i E_i I_i + 6E_s I_s} + \frac{2}{\sum_i E_i I_i + 4E_s I_s} + \frac{1}{\sum_i E_i I_i + 2E_s I_s} \right) \quad (17)$$

with the bend radius of each segment being

Segment I   $r = \frac{\sum E_i I_i}{Pe} \left[ 1 + 2 \frac{E_s I_s}{\sum E_i I_i} \right]$   (18)

Segment II   $r = \frac{\sum E_i I_i}{2Pe} \left[ 1 + 4 \frac{E_s I_s}{\sum E_i I_i} \right]$ Segment III   $r = \frac{\sum E_i I_i}{3Pe} \left[ 1 + 6 \frac{E_s I_s}{\sum E_i I_i} \right]$

EXAMPLE 2–Moments $M^I$ and $M^{II}$ actuated, $M^{III}=0$.

With loads applied over segments I and II the resulting total deflection angle is given by $$\Phi = \Phi_{11} + \Phi_{12} + \Phi_{13} + \Phi_{21} + \Phi_{22} \quad (19)$$

or $$\Phi = \frac{L}{3} Pe \left( \frac{2}{\sum_i E_i I_i + 6E_s I_s} + \frac{2}{\sum_i E_i I_i + 4E_s I_s} + \frac{1}{\sum_i E_i I_i + 2E_s I_s} \right) \quad (20)$$

and segmental radius' given by

Segment I   $r = \frac{\sum E_i I_i}{Pe} \left[ 1 + 2 \frac{E_s I_s}{\sum E_i I_i} \right]$   (21)

Segment II   $r = \frac{\sum E_i I_i}{2Pe} \left[ 1 + 4 \frac{E_s I_s}{\sum E_i I_i} \right]$ Segment III   $r = \frac{\sum E_i I_i}{2Pe} \left[ 1 + 6 \frac{E_s I_s}{\sum E_i I_i} \right]$

EXAMPLE 3—Moments $M^{II}$ and $M^{III}$ actuated, $M^I=0$.

In the case where loads are applied to segments II and III, the deflection angle is defined by $$\Phi = \frac{L}{3} Pe \left( \frac{2}{\sum_i E_i I_i + 6E_s I_s} + \frac{1}{\sum_i E_i I_i + 4E_s I_s} \right) \quad (22)$$

and the segment bend radius' by

Segment I   $r = \infty$   (23)

Segment II   $r = \frac{\sum E_i I_i}{Pe} \left[ 1 + 4 \frac{E_s I_s}{\sum E_i I_i} \right]$ Segment III   $r = \frac{\sum E_i I_i}{2Pe} \left[ 1 + 6 \frac{E_s I_s}{\sum E_i I_i} \right]$ The relationship between the deflection angle $\Phi$ and the load P for the case of three moments acting simultaneously and distributed evenly along the deflectable portion of the tubular device is presented in EXAMPLE 1. This relationship can be generalized to $$\Phi = Pe \frac{L}{n} \left[ \sum_j^n \left( \frac{j}{\sum E_i I_i + 2jE_s I_s} \right) \right] \quad (24)$$

for a total of n segments and all segments j having moments acting on them. Solving for load P gives $$P = \frac{\Phi}{eL} n \sum_j^n \left[ \frac{\sum E_i I_i + 2jE_s I_s}{j} \right] \quad (25)$$

The load P must be carried by each of the actuated wires in order to achieve the deflection angle $\Phi$ of the deflectable portion of the tubular device. The transmission of load P imparts a tensile stress $\sigma_s$ on each wire equal to $$\sigma_s = \frac{P}{A_s} \quad (26)$$

where $A_s$ is the cross sectional area of the each wire. Substituting equation (26) into equation (25) gives a relation between the stress on each wire and the deflection angle $\Phi$.

$$\sigma_s = \frac{\Phi}{A_s eL} \, n \sum_j^n \left[ \frac{\Sigma E_i I_i + 2j E_s I_s}{j} \right] \quad (27)$$

For the number of segments n=1, this relation reduces to $$\sigma_s = \frac{\Phi}{A_s eL} (\Sigma E_i I_i + 2 E_s I_s) \quad (28)$$

which is similar to equation (9) using equation (24). In both equation (27) and (28) it is seen that the stress developed in the wires while achieving a deflection $\Phi$ is directly proportional to the rigidity of the tubular device and all components contained within (expressed in terms of E and I) and inversely proportional to the length L of the deflectable portion, the eccentricity e of the applied load and the cross sectional area $A_s$ of the loading carrying wires.

By employing multiple load carrying wires, as proposed here, larger deflection angles than would be achieve utilizing a single wire system are obtainable. This is done by controlling of the stress in the load wire by distributing the moments acting on the deflectable portion of the catheter or endoscope. This will be clearer through the following example.

In order to minimize the calculations without loss of generality let us make the following assumption. Let's limit the number of segments n utilized and keep the cross sectional dimensions of the load carry wires small in comparison to the cross sectional dimensions of the tubular device such that the rigidity of the load carrying wires is much less than the accumulated rigidity of the tubular structure or $$2jE_s I_s \ll \Sigma E_i I_i \quad (29)$$

then equation (27) simplifies to $$\sigma_s = \frac{\Phi \Sigma E_i I_i}{A_s eL} \left( \frac{n}{\Sigma j} \right) \quad (30)$$

If n, the number of segments is greater than 1, then the load per wire is reduced as compared to a single loading wire of the same cross sectional area by a factor of $$\left( \frac{n}{\Sigma j} \right) < 1 \quad (31)$$

If $\sigma_o$ is the stress induced in a one wire deflecting system, then by dividing the deflectable portion of the tubular device into n segments and providing each segment with its own means of loading, the stress per wire would be reduced to:

| Number of segments | 1 | 2 | 3 | 4 | n |
|---|---|---|---|---|---|
| Stress per wire | $\sigma_o$ | $(2/3)\sigma_o$ | $(1/2)\sigma_o$ | $(2/5)\sigma_o$ | $(n/\Sigma j)\sigma_o$ |

It could be argued that a corresponding decrease in stress could be accomplished in a single wire system by increasing the wire cross section area. Doing so, however, also increases the rigidity and the dimension of the wire at the expense of other components encased within the tubular device.

An assumption made in the example given is that the cross sectional area of the multiple wires was the same as that of a single wire. This can be accomplished by changing the geometry of the wire such as by utilizing flat wires in place of round wires of comparable cross sectional area.

Alternatively, since by distributing moments, wire stresses are reduced, it is possible to replace larger dimensional wires of suitable strength with smaller distributed wires with no loss of function.

The present invention thus discloses an endoscope capable of deflecting a viewing tip between a neutral position and a plurality of angularly disposed positions. A control mechanism causes deflection of the viewing tip by differentially displacing two sets of operating wires which are operatively connected to a distal controllably bendable section. Each set of operating wires includes a plurality of wires which terminate at different locations along the length of the controllably bendable section thus reducing the load required for each wire to generate a predetermined deflection of the tip.

Although this invention is described in terms of certain preferred embodiments, other embodiments that will be apparent to those of ordinary skill in the art are also within the scope of this invention. Accordingly, the scope of the invention is intended to be defined by the claims that follow.

I claim:

1. A remotely deflectable non-rigid tubular device, having a flexible steering section at a distal end along a longitudinal axis, the steering section comprising:

a hollow flexible tubular member; and a plurality of axially aligned actuating wires radially stacked and contained within said tubular device and attached along a first longitudinal side of said tubular member at axially spaced locations, said locations being radially spaced from the longitudinal axis of said tubular member and substantially in a single plane intersecting said axis so as to divide said steering section into a plurality of deflectable segments, wherein a cross-section of each of said actuating wires has a first area moment of inertia for bending about a first axis perpendicular to said longitudinal axis which is substantially less than a second area moment of inertia of said cross-section about a second axis perpendicular to both said first axis and said longitudinal axis.

2. The deflectable device as in claim 1, wherein said tubular member is a stainless steel variable pitch helical spring and wherein said actuating wires attach to closely wound regions of said spring which are separated by loosely wound regions.

3. The deflectable device as in claim 2, wherein said variable pitch helical spring includes at least one axial spine attached to the closely wound regions along a neutral bending axis of said flexible section.

4. The deflectable device as in claim 1, wherein said tubular member is a stainless steel coil ribbon.

5. The deflectable device as in claim 1, wherein a distal tip forming a terminal end of said steering section is deflected by an angle equal to the sum of deflection angles of said plurality of deflectable segments due to axial displacements of said actuating wires.

6. The deflectable device as in claim 1, wherein said actuation wires have an area moment of inertia about said first axis for bending in said single plane which is less than 0.1 of said second area moment of inertia about said second axis.

7. The deflectable device as in claim 6, wherein said actuation wires have an area moment of inertia about said first axis for bending in said single plane which is less than 0.01 of said second area moment of inertia about said second axis.

8. The deflectable device of claim 1, wherein said actuating wires comprise ribbons having narrow dimensions aligned with said single plane.

9. The deflectable device of claim 1, wherein said actuating wires are enclosed in a flexible oval-shaped sheath along the length of said tubular device which closely surrounds said wires.

10. The deflectable device of claim 9, wherein said flexible sheath comprises an oval-shaped coil wire.

11. The deflectable device of claim 1, further comprising a second set of actuating wires axially disposed and attached to a second side of said tubular member diametrically opposite said first longitudinal side at axially spaced locations similar to said first set of actuating wires, said locations being radially spaced from the longitudinal axis and substantially in said single plane, wherein said deflectable segments may be deflected in a second direction in said single plane.

12. The deflectable device of claim 1, wherein the device is an endoscope comprising:

a coherent fiber optic image bundle, an illumination fiber and a working channel tubing extending through the tubular device and steering section; and a control member attached to a proximal end of said endoscope containing a control mechanism capable of sequentially pulling said actuation wires to cause said deflectable segments of said steering section to deflect at different times.

13. The endoscope as in claim 12, wherein said control mechanism comprises:

a plurality of stacked plates having different sized aligned slots; and an actuation pin extending through said slots, wherein each of said plurality of actuation wires is attached to one plate and wherein translation of said pin causes sequential translation of said plates due to said different sized slots.

14. A deflectable endoscope, comprising:

a distal insertion tube;

a proximal end attached to said insertion tube;

a distal flexible portion on said insertion tube comprising a hollow flexible tubular member;

a plurality of axially aligned and radially stacked actuating wires extending from said proximal end along said insertion tube attached to said tubular member at axially spaced locations so as to segment said flexible portion;

coherent fiber optic image bundle, means for illumination and a working channel extending from said proximal end through said insertion tube and tubular member; and means on said proximal end of said endoscope for sequential loading of said actuating wires wherein sequential loading of said actuating wires produces a segmentalized deflection of said flexible portion in a bending plane.

15. The endoscope as in claim 14, wherein said tubular member is a stainless steel variable pitch helical spring and wherein said actuating wires attach to closely wound regions of said spring which are separated by loosely wound regions.

16. The endoscope as in claim 15, wherein said variable pitch helical spring includes at least one axial spine attached to the closely wound regions along a neutral bending axis of said flexible portion.

17. The endoscope as in claim 14, wherein said tubular member is a stainless steel coil ribbon.

18. The endoscope as in claim 14, wherein said actuating wires are substantially less rigid in said bending plane of the endoscope than in any other plane aligned with a longitudinal axis of said flexible portion.

19. The endoscope of claim 14, wherein a cross section of said actuating wires comprises a rectangular shape with a narrow dimension aligned with said bending plane.

20. The endoscope of claim 14, wherein said actuating wires are enclosed in a flexible oval-shaped sheath which closely surrounds said wires from said proximal end to said flexible portion.

21. The endoscope of claim 20, wherein said flexible sheath comprises an oval-shaped coil wire.

22. A remotely deflectable tubular non-rigid endoscope, wherein deflection of a flexible distal portion is achievable by a sequential axial loading of various segments of said distal flexible portion of the endoscope, comprising:

a plurality of radially stacked actuating wires passing axially through an interior of said endoscope and attached to said flexible portion of said endoscope so as to axially segment said flexible portion;

means provided at a proximal end of said endoscope for sequentially axially loading said actuating wires, wherein sequential loading of said actuating wires effects a remote deflection of said flexible portion of said endoscope by providing moments distributed along the axial length of said flexible portion of said endoscope; and a coherent fiber optic image bundle, an illumination fiber and a working channel tubing extending through the endoscope and flexible portion.

23. A method of deflecting an elongated tubular device, comprising the steps of:

stacking a plurality of wires within said tubular device along a longitudinal axis such that said wires collectively stacked are substantially less rigid in a desired bending plane of the tubular device parallel to said longitudinal axis than in any other plane parallel to said longitudinal axis;

attaching a distal end of each of said plurality of wires to axially spaced points along a distal flexible steering portion of said device; and axially loading said plurality of wires to cause deflection of said flexible steering portion.

24. The method of deflecting a tubular device as in claim 23, wherein said axial loading of each of said plurality of wires occurs sequentially.

25. The method of deflecting a tubular device as in claim 24, wherein said sequential loading includes the steps of:

attaching proximal ends of said plurality of wires to a control mechanism such that actuating a single member causes sequential displacement of said proximal ends.

26. The method of deflecting a tubular device as in claim 25, wherein said sequential loading includes the steps of:

attaching said proximal ends of said plurality of wires to a series of parallel stacked plates having differentially sized slots;

passing an actuation pin transversely through said slots; and linking the motion of said single member to said pin such that actuation of said single member causes said pin to translate parallel to said plates thus first moving one of said plates having a smallest slot and an attached wire when said pin contacts an inner edge of said smallest slot, and subsequently moving each of said plates and correspondingly attached wires in an ascending order of said differentially sized slots.

27. The method of deflecting a tubular device as in claim 23, further comprising the step of:

providing a coherent fiber optic image bundle, an illumination fiber and a working channel extending from said control mechanism to a distal tip of said flexible steering portion.

28. A remotely deflectable non-rigid tubular endoscope, having a flexible steering section at a distal end along a longitudinal axis, said endoscope including:

a coherent fiber optic image bundle, an illumination fiber and a working channel tubing extending from said proximal end through said endoscope and steering section; said steering section comprising:

a hollow flexible tubular member; and a plurality of axially aligned actuating wires contained within said endoscope, the wires being radially stacked toward the longitudinal axis of said endoscope, said actuating wires capable of applying an axial force to a plurality of axially spaced locations along said steering section for deflecting said endoscope.

29. The endoscope of claim 28, wherein said plurality of axially aligned actuating wires are attached along a first longitudinal side of said tubular member at axially spaced locations, said locations being radially spaced from the longitudinal axis of said tubular member and substantially in a single plane intersecting said axis so as to divide said steering section into a plurality of deflectable segments, wherein a cross-section of each of said actuating wires has a first area moment of inertia for bending about a first axis perpendicular to said longitudinal axis which is substantially less than a second area moment of inertia of said cross-section about a second axis perpendicular to both said first axis and said longitudinal axis.

30. The endoscope of claim 28, further comprising:

means on said proximal end of said endoscope for sequential loading of a plurality of actuating wires attached at axially spaced locations along said tubular member so as to divide said steering section into a plurality of deflectable segments wherein loading of said actuating wires produces a segmentalized deflection of said steering section in a desired bending plane.

31. The endoscope of claim 30, wherein said loading means comprises:

a control mechanism capable of sequentially pulling said actuating wires to cause said deflectable segments of said steering section to deflect at different times.

32. The endoscope of claim 31, wherein said control mechanism comprises:

a plurality of stacked plates having different sized aligned slots; and an actuating pin extending through said slots, wherein each of said plurality of actuation wires is attached to one plate and wherein translation of said pin causes sequential translation of said plates due to said different sized slots.

33. A remotely deflectable non-rigid tubular endoscope, having a flexible steering section at a distal end along a longitudinal axis, the steering section comprising:

a hollow flexible tubular member comprising a stainless steel variable pitch helical spring;

a plurality of axially aligned actuating wires contained within said endoscope and attached along a first longitudinal side of said tubular member at axially spaced locations, said actuating wires attach to closely wound regions of said spring which are separated by loosely wound regions, said axially spaced locations being radially spaced from the longitudinal axis of said tubular member and substantially in a single plane intersecting said axis so as to divide said steering section into a plurality of deflectable segments, wherein a cross-section of each of said actuating wires has a first area moment of inertia for bending about a first axis perpendicular to said longitudinal axis which is substantially less than a second area moment of inertia of said cross-section about a second axis perpendicular to both said first axis and said longitudinal axis; and a coherent fiber optic image bundle, an illumination fiber and a working channel tubing extending through the endoscope and steering section.

34. The deflectable endoscope as in claim 33, wherein said variable pitch helical spring includes at least one axial spine attached to the closely wound regions along a neutral bending axis of said flexible steering section.

35. A remotely deflectable non-rigid tubular endoscope, having a flexible steering section at a distal end along a longitudinal axis, the endoscope comprising:

a hollow flexible tubular member in said steering section;

a plurality of axially aligned actuating wires contained within said tubular endoscope and attached along a first longitudinal side of said tubular member at axially spaced locations, said locations being radially spaced from the longitudinal axis of said tubular member and substantially in a single plane intersecting said axis so as to divide said steering section into a plurality of deflectable segments, wherein a cross-section of each of said actuating wires has a first area moment of inertia for bending about a first axis perpendicular to said longitudinal axis which is substantially less than a second area moment of inertia of said cross-section about a second axis perpendicular to both said first axis and said longitudinal axis;

a coherent fiber optic image bundle, an illumination fiber and a working channel tubing extending through the tubular device and steering section; and a control member attached to a proximal end of said endoscope containing a control mechanism capable of sequentially pulling said actuation wires to cause said deflectable segments of said steering section to deflect at different times, wherein said control mechanism comprises:

a plurality of stacked plates having different sized aligned slots; and an actuation pin extending through said slots, wherein each of said plurality of actuation wires is attached to one plate and wherein translation of said pin causes sequential translation of said plates due to said different sized slots.

36. A remotely deflectable non-rigid tubular endoscope, having a flexible steering section at a distal end along a longitudinal axis, the endoscope comprising:

a hollow flexible tubular member in said steering section;

a plurality of axially aligned actuating wires contained within said endoscope and attached along a first longitudinal side of said tubular member at axially spaced locations, said locations being radially spaced from the longitudinal axis of said tubular member and substantially in a single plane intersecting said axis so as to divide said steering section into a plurality of deflectable segments, wherein a cross-section of each of said actuating wires has a first area moment of inertia for bending about a first axis perpendicular to said longitudinal axis which is substantially less than a second area moment of inertia of said cross-section about a second axis perpendicular to both said first axis and said longitudinal axis;

a coherent fiber optic image bundle, an illumination fiber and a working channel tubing extending through the tubular endoscope; and a control member attached to a proximal end of said endoscope containing a control mechanism having a single control handle, wherein actuation of said single control handle sequentially pulls said actuation wires to cause said deflectable segments of said steering section to deflect at different times.

* * * * *